(12) United States Patent
Manners et al.

(10) Patent No.: US 6,565,992 B1
(45) Date of Patent: May 20, 2003

(54) PHOSPHORESCENT OXYGEN SENSORS

(76) Inventors: Ian Manners, 2142 Margot St., Oakville, Ontario (CA), L6H 3M1; Xijia Gu, 113 Marrbury Cresc, North York, Ontario (CA), M3A 2G3; Zhen Pang, 773 Dovercourt Road, Toronto, Ontario (CA), M6H 1X2; Mitchell A. Winnik, 486 Glen Lake Avenue, Toronto, Ontario (CA), M6P 1G8; Yizeng Ni, 616c Hibbard Dr., Chapel Hill, NC (US) 27514

( * ) Notice: Subject to any disclaimer, the term of this patent is extended or adjusted under 35 U.S.C. 154(b) by 0 days.

(21) Appl. No.: 09/189,437

(22) Filed: Nov. 10, 1998

(Under 37 CFR 1.47)

Related U.S. Application Data

(63) Continuation-in-part of application No. 08/642,527, filed on May 3, 1996, now abandoned.

(51) Int. Cl.$^7$ .............................................. G01N 21/00
(52) U.S. Cl. ...................... 428/690; 436/136; 436/172; 73/29.03; 73/31.01; 73/31.05; 73/384; 250/484.4; 252/301.16; 252/301.35
(58) Field of Search ................................ 73/384, 29.01, 73/29.03, 31.01, 31.05; 252/301.16, 301.35; 428/690; 250/484.4; 436/136, 138, 172

(56) References Cited

U.S. PATENT DOCUMENTS

| | | | |
|---|---|---|---|
| 4,994,396 A | * 2/1991 | Lefkowitz et al. | 436/136 |
| 5,151,603 A | 9/1992 | Nakamura | 250/458.1 |
| 5,173,432 A | * 12/1992 | Lefkowitz et al. | 436/138 |
| 5,359,887 A | 11/1994 | Schwab et al. | 73/147 |
| 5,652,067 A | * 7/1997 | Ito et al. | 428/690 |

FOREIGN PATENT DOCUMENTS

| | | |
|---|---|---|
| CA | CDA 2204319 | 11/1998 |
| CA | CDA 2227309 | 7/1999 |
| EP | 0 536 480 A2 | 7/1992 |

OTHER PUBLICATIONS

Phosphorescent Oxygen Sensors . . . Polymer Matrices Pang et al. Advanced Materials. 1998, 8 No. 9., pp. 768–771. (No month).
Polymers with Sulfur . . . Ni et al. Macromolecules 1996, 29, pp. 3401–3408. (No month).
Inorganic–Organic Polymers H.R. Allcock. Advanced Materials 1994, 6. No2., pp. 106–115. (No month).
Sulfur . . . Polymers I. Manners. Coordination Chemistry Reviews 1994, 137, pp. 109–129. (No month).
Poly(alkyl/aryloxothiazenes): . . . Calculations Roy et al. J. Am. Chem. Soc. 1993, 115, pp. 2604–2612. (No month).
Synthesis, Glass . . . at Sulfur Ni et al., Macromolecular/Am Chem Soc./ 1992, 25, pp. 7119–7125. (No month).
Poly(thionylphosyhazenes): . . . Atoms, Liang & Manners. J. Am. Chem. Soc. 1991, 113, pp. 4044–4045 (No month).
Poly(thionylphophazenes) . . . Fluoropolymers–2 Pages Liang & Manners Makromol. Chem. Commun. 12, 1991, pp. 613–616. (No month).

\* cited by examiner

*Primary Examiner*—Marie Yamnitzky
(74) *Attorney, Agent, or Firm*—Thomas A. O'Rourke; Bodner & O'Rourke

(57) ABSTRACT

A pressure sensor comprising a stable polymer having a backbone containing nitrogen and one or more of sulfur or phosphorous, and including a phosphorescent dye agent.

47 Claims, 11 Drawing Sheets

Synthesis of Poly[(methylamino)thionylphosphazene] - b - Poly(tetrahydrofuran) Block Copolymer

SCHEME 1

$^1$H NMR OF A MECHANICAL BLEND OF 1 AND 5c (A) AND $^1$H NMR OF THE PRECIPITATION PRODUCT THAT WAS ISOLATED (B), POLY (THF).

$^1$H NMR OF 5c (A) AND $^1$H NMR OF THE PRECIPITATION PRODUCT THAT WAS ISOLATED (B).

AIR-QUENCHING INTENSITY DATA FOR 1000 ppm OF [Ru(4,7-DIPHENYLPHEN)$_3$] Cl$_2$ IN POLYMER 5b. THE SOLID LINE IS OBTAINED FROM THE BEST FIT USING THE STERN-VOLMER MODEL.

PHOSPHORESCENT OXYGEN SENSORS

REFERENCE TO CO-PENDING APPLICATION

This is a Continuation-In-Part application of application Ser. No. 08/642,527 filed May 3, 1996, now abandoned, the subject matter of which is incorporated herein by reference.

BACKGROUND OF THE INVENTION

1. Field of the Invention

The present invention relates to pressure sensors, more particularly phosphorescent oxygen sensors and more particularly to compositions for forming pressure sensors and coatings therefor.

2. Description of the Related Art

The field of luminescent barometry has developed as a result of continuing difficulties encountered with other mechanical means to measure pressure distributions over aerodynamic surfaces. The theories of luminescent barometry are described in detail in U.S. Pat. No. 5,359,887 and U.S. Pat. No. 5,151,603. Luminescent barometry is based on the phenomenon that some phosphorescent materials emit light at a unique wavelength and which is 'quenched' by the presence of particular molecules such as oxygen. This quenching effect can be quantified so that the phosphorescent material, provided in an oxygen permeable matrix can be used to mere, for example, the partial pressure of oxygen passing over aerodynamic surfaces.

As a consequence of their considerable fabrication advantages, the use of polymers for the construction of sensing devices using this quenching effect is an area of intense current interest. Luminescent sensors based on composites comprising transition metal phosphorescent dyes immobilized in polymer matrices have attracted attention as oxygen sensors for both biomedical and barometric applications. Conventional phosphors dyes such as Pt (platinum) octaethylporphyrin (OEP) derivatives or $Ru^{II}$ (ruthenium) bipyridyl (bipy) or phenanthroline (Phen) derivatives with oxygen quenchable excited states have bee dispersed in a silicone (otherwise known as polysiloxane) based polymer matrices due to their high gas permeability.

However, these conventional silicone-based polymer systems tend to be incompatible with the dyes and can lead to undesirable local concentrations and thus reduced sensitivity. Most PtOEP based systems in cross-linked silicone polymer matrices also have non-linear dependence on air pressure thereby making measurements less accurate.

More importantly, conventional polysiloxane coatings tend to continue cross-linking with time or as their temperature rises which causes irreversible changes in their phosphorescent properties as a result, making their data subject to error and generally unsuitable for measurements taken in fluctuating temperature conditions.

It is therefore an object of the present invention to provide a novel pressure sensor.

It is a further object of the present invention to provide novel compositions for pressure sensors.

It is a further object of the present invention to provide novel compositions for use as phosphorescent sensors.

It is a further object of the present invention to provide novel composition for use as phosphorescent sensors and which provide improved sensitivity, linearity, or repeatability.

SUMMARY OF THE INVENTION

In one of its aspects, the invention involves a pressure sensor comprising a stable polymer having a backbone containing nitrogen and one or more of sulfur or phosphorous, and including a phosphorescent dye agent.

Preferably, the backbone contains both phosphorous and sulfur. More preferably, the sulfur is in the form of sulfur VI, the sulfur and phosphorus have side groups selected from the group consisting of oxygen, a halogen, an aryloxy group, an alkoxy group, an arylamine group and an alkamine group.

More preferably, the sulfur has a first side group including oxygen and a second side group including a halogen.

In another preferred embodiment, the sulfur has a second side group, the phosphorous has first and second side groups which may be the same as or different from one another and from second side group on sulfur and are each selected from $NHBu^n$, $OBu^n$, $OC_6H_4$, $OC_6H_4CF_3$—m $OCH_2CH=CH_2$ and $OC6H_4,CF_3$—p.

In another of its aspects, the present invention provides a pressure sensor comprising a stable polymer having a backbone containing nitrogen and one or more of sulfur or phosphorous, and including a phosphorescent dye agent, the polymer including therein a phosphorescent dye agent, wherein the polymer has a glass transition temperature ranging from −20° C. to 0° C. More preferably, the polymer has a glass transition temperature ranging from −17° C. to 0° C., more particularly about −17° C.

In yet another aspect of the present invention, there is provided a pressure sensor comprising a stable polymer having a backbone containing nitrogen and one or more of sulfur or phosphorous, and including a phosphorescent dye agent. Preferably, the polymer and dye agent are in the form of a coating.

Preferably, pressure sensors made according to the present invention are operatively characterized by a Stern Volmer plot having a linearity ranging from 0.980 to 1.0, more preferably 0.985 to 0.995, and still more preferably 0.990 to 0.995. Alternatively, pressure sensors made according to the present invention may preferably be operatively characterized by a Stern Volmer plot having a linearity ranging from 0.989 to 0.999, still more preferably 0.996 to 0.999.

Still more preferably, pressure sensors made according to the present invention are operatively characterized by a Stern Volmer plot having one or more of the above linearity ranges and over a range of pressures, namely from about 0.1 to 75 psi more preferably 0.1 to 50 psi, still more preferably 0.2 to 40 psi.

In another aspect of the present invention, there is provided a pressure sensor comprising a stable polymer having a backbone containing nitrogen and one or more of sulfur or phosphorous, and including a phosphorescent dye agent, wherein the polymer is a first polymer block in a block copolymer. Preferably, the first polymer block includes both sulfur and phosphorous and terminates at the sulfur in an electron deficient state, and the copolymer includes a second polymer block having a backbone which includes at least one electron rich site.

Preferably, the sulfur is sulfur VI and the at least one electron rich site includes oxygen or nitrogen. More preferably, the second polymer block is formed by a ring opening polymerization of a heterocyclic group in the presence of the first polymer block and the heterocyclic group is selected from the group comprising a substituted $C_{3-20}$ cycloalkyl group, a substituted $C_{6-20}$ aryl group and a substituted or unsubstituted $C_{6-20}$ aralkyl group. Still more preferably, the heterocyclic group is a $C_{3-5}$ cyclic group with the oxygen or nitrogen substituent therein such as tetrahydrofuran, ethylene oxide or propylene oxide.

In another aspect, the invention involves a phosphorescent oxygen sensor comprising a substrate having a surface, a polymer as define above being applied to the surface to form a coating.

In still another aspect of the present invention, there is provided a method of forming a pressure sensor, comprising the steps of:

forming a mixture including a polymer having a backbone containing nitrogen and one or more of sulfur and phosphorous, together with a phosphorescent dye agent; and applying the mixture to a substrate.

In another of its aspects, the present invention provides a pressure sensor comprising a first stable polymer block having a backbone containing nitrogen and one or more of sulfur and phosphorous, and terminating at the sulfur in an electron deficient state, and a second polymer block having a backbone which includes at least one electron rich site, the pressure sensor further comprising a phosphorescent dye agent.

In another of its aspects, here is provided a method of fob a pressure sensor comprising the steps of:

providing a first stable polymer block having a backbone containing nitrogen and one or more of sulfur and phosphorous, and carrying out a ring opening polymerization of an unsaturated heterocyclic group having at least one electron rich site therein, thereby to form a copolymer, and mixing the copolymer with a phosphorescent dye agent.

Preferably, the ring opening polymerization step is carried out in the presence of the first polymer block. More preferably, the heterocyclic group is selected from the group comprising a substituted $C_{3-20}$ cycloalkyl group, a substituted $C_{6-20}$ aryl group and a substituted or unsubstituted $C_{6-20}$ aralkyl group. Still more preferably, the heterocyclic group is a $C_{3-5}$ cyclic group with the oxygen or nitrogen substituent therein. Still more preferably, the heterocyclic group is tetrahydrofuran, ethylene oxide or propylene oxide.

In still another of its aspects, the present invention provides a pressure sensor comprising a polymer of formula A, wherein:

E1, E2 and E3 are the same or are different and are selected from either sulfur or phosphorus;

R1 to R6 are either the same or different and are selected from the group comprising oxygen, a halogen, hydrogen, methyl a substituted or unsubstituted $C_{2-20}$ linear or branched alkyl group, a substituted or unsubstituted $C_{2-20}$ linear or branched alkenyl group, a substituted or unsubstituted $C_{2-20}$ linear or branched alkynyl group, a substituted or unsubstituted $C_{6-20}$ aryl group, a substituted or unsubstituted $C_{3-20}$ cycloalkyl group; and the pressure sensor further comprising a phosphorescent dye agent.

Preferable, E1 is sulfur VI and E2 and E3 are each phosphorus, each of R2 to R6 includes an oxygen or a nitrogen substituent.

More preferably, each of R3 to R6 is an aryloxy group, an arylamine group, alkoxy group or an alkamine group. Still more preferably, each of R3 to R6 is selected from the group consisting of $NHBu^n$, $OBu^n$, $OC_6H_4$, $OC_6H_4CF_3$—m and $OCH_2CH=CH_2$.

The R2 is preferably a halogen or the same as or different from R3 to R6. In one embodiment, R2 and R3 to R6 are each $NHBu^n$.

In still mother of its aspects, the present invention provides a pressure sensor comprising a copolymer of the formula B wherein E1, E2 and E3 are the same or are different and are selected from either sulfur or phosphorus;

R1 to R6 are either the same or different and are selected from the group comprising oxygen, a halogen, hydrogen, methyl a substituted or unsubstituted $C_{2-20}$ linear or branched alkyl group, a substituted or unsubstituted $C_{2-20}$ linear or branched alkenyl group, a substituted or unsubstituted $C_{2-20}$ linear or branched aryl group, a substituted or unsubstituted $C_{6-20}$ aryl group, a substituted or unsubstituted $C_{3-20}$ cycloalkyl group, R7 is selected from oxygen, nitrogen or from groups 15 and 16 of the periodic table of elements, R8 is selected from the group comprising methylene, a substituted or unsubstituted $C_{2-20}$ linear or branched alkyl group, a substituted or unsubstituted $C_{2-20}$ linear or branched alkenyl group, a substituted or unsubstituted $C_{2-20}$ linear or branched alkynyl group, a substituted or unsubstituted $C_{6-20}$ aryl group, a substituted or unsubstituted $C_{3-20}$ cycloalkyl group; and the pressure sensor further comprising a phosphorescent dye agent.

Preferably, R7 is oxygen, nitrogen or sulfur and R3 to R6 are each selected from the group consisting of $NHBu^n$, $OBu^n$, $OC_6H_4$, $OC_6H_4CF_3$—m, $OCH_2CH=CH_2$ and $OC_6H_4CF_3$—p. Still more preferably, R2 is a halogen or is the same as R3 to R6.

BRIEF DESCRIPTION OF THE DRAWINGS

Several preferred embodiments of the present invention will be provided, by way of example only, with reference to the appended drawings, wherein.

DESCRIPTION OF THE PREFERRED EMBODIMENTS

Figure 1:
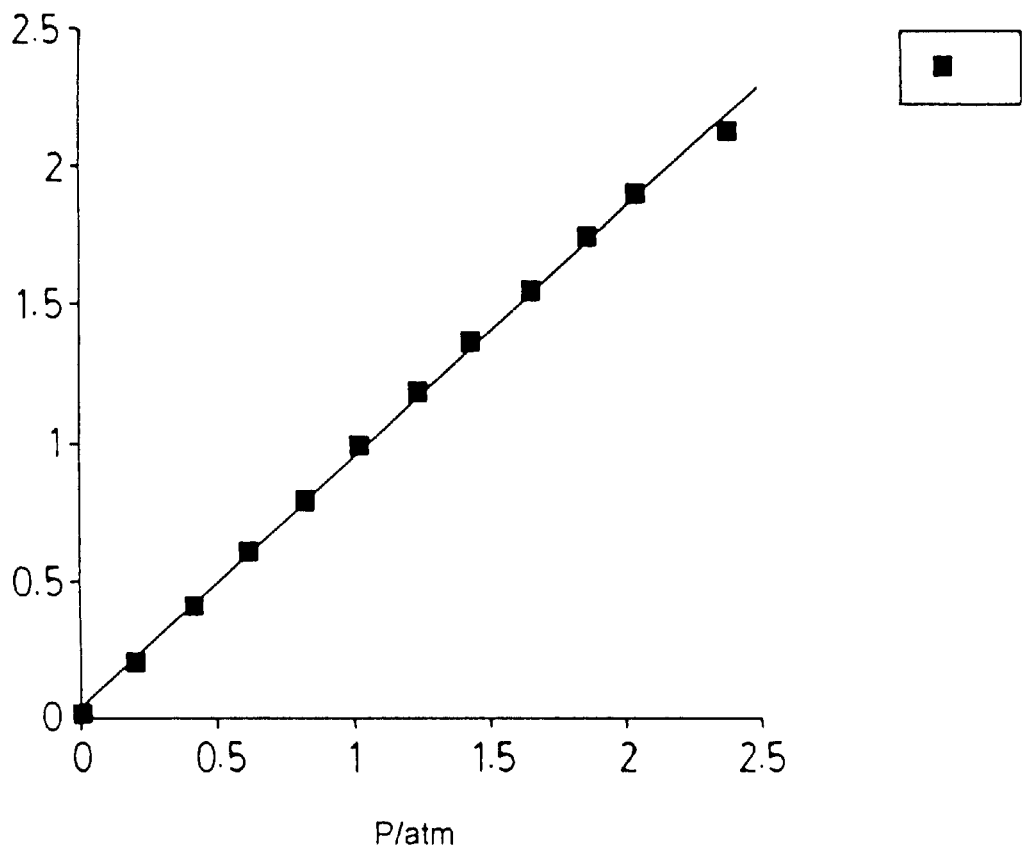
FIG. 1 is a plot of a Luminescence Intensity Ratio versus pressure for one exemplified polymer.

The invention involves a polymer coating formed from a polymer which itself includes a phosphorescent dye agent contained in a polymer, the latter of which having the formula A wherein:

E1, E2 and E3 are the same or are different and are selected from either sulfur or phosphorus;

R1 to R6 are either the same or different and are selected from the group comprising oxygen, a halogen, hydrogen, methyl a substituted or unsubstituted $C_{2-20}$ linear or branched alkyl group, a substituted or unsubstituted $C_{2-20}$ linear or branched alkenyl group, a substituted or unsubstituted $C_{2-20}$ linear or branched alkynyl group, a substituted or unsubstituted $C_{6-20}$ aryl group, a substituted or unsubstituted $C_{3-20}$ cycloalkyl group.

The polymer A provides particular advantages as a constituent in pressure sensors, preferably phosphorescent oxygen sensors and coatings therefor. The polymer A is polar, owing to the presence of electron rich sites in its backbone, and allows for improved distribution of the dye agent, in turn providing improved sensitivity.

The constituents should be selected having regard to the oxygen environment in which the sensing is to take place and in particular the expected temperature ranges in which the sensor so formed is to be expected to be operable and this may be measured by the Glass Transition Temperature ($T_g$), and which may be considered as the boundary of the temperatures substantially above which there is sufficient permeability for gases such as oxygen.

Preferably, E1 is sulfur VI and R1 is oxygen, while each of E2 and E3 are phosphorus, providing a repeating PN segment in the backbone along with an oxygen side group on sulfur forming a relatively small terminating S=O segment. The S=O segment contributes an asymmetry to the backbone to discourage crystalization, which is sensitive to the regularity of the polymer chain. Moreover, the S=O segment contributes to an amorphous structure which is a contributing factor to the gas permeability of resulting polymers.

In still another aspect of the present invention, there is provided a method of forming a phosphorescent oxygen sensor, comprising the steps of forming a solvent mixture including a polymer having a backbone containing nitrogen and one or more of sulfur or phosphorous and a phosphorescent dye agent; and applying the mixture to a substrate.

For example, the polymer can be formed by polymerizing a thionylphosphazene from its cyclic form to a linear form, for example with halogenated side groups using the technique disclosed in Y. Ni et al (MACROMOLECULES 1992, 27, 7119), the subject matter of which is incorporated herein by reference, and later establishing the appropriate side chains, for example by substituting one or more of the halogenated side groups, according to the characteristics desired in the resulting polymer.

More preferably, each of R2 to R6 includes an oxygen or a nitrogen substituent and each of R2 to R6 may be provided in the form of an aryloxy group, an alkoxy group, arylamine group or an alkamine group and may include therein a phenyl group. In this case, the aryloxy and the arylamine tend to increase $T_G$ due to the fact that these groups tend to be relatively more rigid. In contrast, the alkoxy and alkamine groups tend to be more flexible, contributing to a lower $T_G$ and higher permeability. In each of the oxy and amine groups, polarity is increased by the presence of oxygen and nitrogen substituents. These oxy and amine groups can be selected with increased polarity by providing for increasing numbers of polar substituents such as oxygen and nitrogen.

If desired the permeability, $T_G$ and polarity can be tailored by the selection, or for that matter, a mixture of groups along the polymer depending on the contribution of each group. In some cases, the choice of the R groups may also influence the polarity of the polymer and thus the interactions between the polymer and the dye agent, leading in some cases to relatively uneven distribution (such as some polymers having fluronated side groups, for example some polymers having one or more trifluroethoxy side groups) and in other cases to relatively fine and even distribution (examples including poly("butylaminothionylphosphazene) 3 and poly ("butylaminothionylphosphazene)-b-poly(tetrahydrofuran) 4. However, the resulting composition, when used as a phosphorescent sensor, requires no cross-linking and therefore should be a desirable advance, in either case.

Mixtures of polymer and dye agent may be suitable with concentrations of dye ranging from 1 ppm to 3000 ppm, preferably 750 to 2000 ppm, still more preferably 1000 ppm, to 1500 ppm.

The polymer should also be formed so that they are stable for their intended use. In this case, the term stable polymer is intended to mean one which is stable in its intended environment, that is for a given period of time, and when subject to certain conditions, such as hydrolysis. For example, it is contemplated that some examples of such polymers, although stable in the short term may in fact be biodegradable, therefore with a planned breakdown beyond its intended useful life. Furthermore, the polymers should also have photo stability, that is be stable within reasonable tolerances to photo irradiation for the purposes of exciting the phosphorescent dye agent. In addition, the polymers should, to some degree depending on their intended life span, be resistant to attack by single oxygen, for example, a byproduct of the quenching process.

In a preferred embodiment, E1 is sulfur and E2, E3 are each phosphorus. In a still further preferred embodiment, each of R2 to R6 are an alkylamine group and synthesis of an exemplified version of this further preferred version of the polymer A is shown by the structures 1 to 3 and involves the thermal ring-opening polymerization of the cyclic monomer 1 followed by treatment of the halogenated polymer 2 with an excess of n-butylamine and is further described below.

The polymer 3 is a hydrolytically stable amorphous elastomeric material and possesses a Tg of –17° C. giving it both relatively high free volume and gas permeability. The polymer can also be formed as a high quality film coating with dimensional stability without the need for cross-linking.

The intensity characteristics of a phosphorescent material are modeled by the Stern-Volmer equation which can be expressed as follows:

$$I_{1.00}/I = A + B(P/P_{1.00}), \text{ where}$$

$I_{1.00}/I$=Luminescence Intensity Ratio (the 'LIR')

I=luminescence intensity, $I_{1.00}$=luminescence intensity at 1.00 atmosphere. (used as a reference);

p=air pressure in atmospheres;

A=Coefficient for vacuum condition;

B=Coefficient corresponding to gradient of curve, or rate of change of the Luminescence Intensity Ratio; and $P_{1.00}$=Reference pressure.

Compositions containing the polymer 3 together with phosphorescent dye agents show well-defined Stern-Volmer behaviour and significantly improved sensitivity.

In yet another aspect of the present invention, there is provided a pressure sensor comprising a stable polymer as defined above and a phosphorescent dye agent. Preferably, the polymer and dye agent are in the form of a coating. More preferably, the pressure sensor is operatively characterized by a Stern Volmer plot having ranging from 0.980 to 1.0. More preferably, the sensor is operatively characterized by a Stern Volmer plot having a linearity ranging from 0.985 to 0.995, still more preferably 0.990 to 0.995. Alternatively, the sensor is operatively characterized by a Stern Volmer plot having a linearity ranging from 0.989 to 1.0, still more preferably 0.996 to 0.999. Still more preferably, the pressure sensors herein can in some cases be operatively characterized by a Stern Volmer plot hang the above linearity ranges and over a range of pressures, namely from about 0.1 to 75 psi more preferably 0.1 to 50 psi, still more preferably 0.2 to 40 psi.

Preferably, the dye agent includes a platinum or a ruthenium substituent. More preferably, the dye agent is selected from the group consisting of Pt octaethylpophyrin, $Ru^{II}$ bipyridyl and $Ru^{II}$ phenanthroline derivatives, though other known organic and inorganic dye agents, both phosphorescent and otherwise, are also contemplated.

Compositions made according to the present invention have been shown to be usable on substrates such as stainless steel and alumina, though other substrates such as glass, plastics and metals are also contemplated.

In still another aspect of the present invention there is provided a copolymer having the formula B wherein:

E1, E2 and E3 are the same or are different and are selected from either sulfur or phosphorus;

R1 to R6 are either the same or dent and are selected from the group comprising oxygen, a halogen, hydrogen, methyl a substituted or unsubstituted $C_{2-20}$ linear or branched alkyl group, a substituted or unsubstituted $C_{2-20}$ linear or branched alkenyl group, a substituted or unsubstituted $C_{2-20}$ linear or branched alkynyl group, a substituted or unsubstituted $C_{6-20}$ aryl group, a substituted or unsubstituted $C_{3-20}$ cycloalkyl group;

R7 is selected from oxygen, nitrogen or from groups 15 and 16 of the periodic table of elements;

R8 is selected from the group comprising methylene, a substituted or unsubstituted $C_{2-20}$ linear or branched alkyl group, a substituted or unsubstituted $C_{2-20}$ linear or branched alkenyl group, a substituted or unsubstituted $C_{2-20}$ linear or branched alkynyl group, a substituted or unsubstituted $C_{6-20}$ aryl group, a substituted or unsubstituted $C_{3-20}$ cycloalkyl group.

The copolymer of the formula B may be formed by first providing a first polymer block of the formula A and then carrying out a ring opening polymerization of an unsaturated heterocyclic group having at least one electron rich site therein. For example, the first polymer block A may be formed as mentioned above, by polymerizing a thionylphosphazene from its cyclic form to a noncyclic form and reacting the noncyclic form with a second polymer block. The noncyclic thionylphosphazene may for example be a halogenated linear thionylphosphazene, whose side groups may be substituted with other groups such as with one or more butylamine groups, for example, before or after the reaction with the second polymer block. Furthermore, the chain length of the copolymer can be adjusted, in some cases, by varying the length of time the first polymer block is exposed to the second polymer block.

Conveniently, the second polymer block can be formed by a ring opening polymerization of a heterocyclic group in the presence of the first polymer block, wherein the heterocyclic group is selected from the group comprising a substituted $C_{3-20}$ cycloalkyl group, a substituted $C_{6-20}$ aryl group and a substituted or unsubstituted $C_{6-20}$ aralkyl group.

More preferably, the heterocyclic group is an unsaturated $C_{3-5}$ cyclic group with the oxygen or nitrogen substituent therein. Still more preferably, the unsaturated heterocyclic group is tetrahydrofuran, ethylene oxide or propylene oxide.

Preferably, E1 is sulfur VI, while E2 and E3 are each phosphorus and R7 is an electron rich site such as sulfur, oxygen, nitrogen or any one of groups 15 or 16 in the periodic table and provides the electron rich site by virtue of their lone pair of unpaired electrons. The electron rich site is thus able to form a stable electron bond with the electron deficient sur and thereby initiate the ring opening polymerization in the presence of the first polymer block.

Preferably, the sulfur in the first polymer block is in a stable form, preferably a hydrolytically stable form, more preferably in the form of sulfur VI in view of the fact that sulfur in other forms such as sulfur IV may be unstable in some cases, such as for example polythiophosphazene. Further examples of unstable sulfur IV polymers may be found in I. Manners (COORDINATION CHEMISTRY REVIEWS, 137, 1994, 109–129), the subject matter of which is incorporated herein by reference.

The copolymer made according to the present invention provides still further improved integrity over conventional polysiloxane polymers and one example of the copolymer is shown at 4. While the polymer 3 may provide the coating with a generally tacky consistency, the copolymer 4 may be used to form a layer of material capable of withstanding its own weight. In other words, the copolymer is envisaged in uses beyond mere coatings but perhaps in the formation or fabrication of devices with an inherent pressure sensing, and preferably phosphorescent oxygen sensing, capability. Moreover, selected ones of the copolymer 4 may be especially useful in such applications as the modeling of air flow over objects such as aircraft or the measuring of oxygen content in ground water, due to the part that the material is capable of a relatively smooth, abrasion resistant surface.

A sample formed from polymer 3 or copolymer 4 with a $T_G$ of $-17°$ C. will typically allow the sample to be used in environments whose temperatures will substantially exceed $-17°$ C., that is where the sample will allow for the permeation of oxygen and hence allow or the subsequent quenching of luminescence.

The present invention provides a coating which provides superior characteristics over those currently available. Like Heir polysiloxane counterparts, the present coatings based on the polymer A or the copolymer B, as illustrated by the preferred examples 3 and 4 respectively, present phosphorescent properties that change with temperature. However, due to the lack of cross linking in the matrix, the repeatability of the data presented by coatings based on the polymer 3 or the copolymer 4 is improved over their polysiloxane counterparts.

The present coatings form improved films with faster drying times and without supplemental curing which is necessary for polysiloxane polymers. The present coatings have improved mechanical integrity and are believed to have substantially no long term flow (creep) on the surface.

Tables 1 to 4 are provided to illustrate a selection of possible groups for R1 to R6 in the polymer of the formula A. These tables are obtained from several published papers, namely I. Manners (COORDINATION CHEMISTRY REVIEWS, 137, 1994, 109–129), the subject matter of which is incorporated herein by reference, and Y. Ni et al (MACROMOLECULES 1992, 27, 7119). It is worth noting that a number of R groups have $T_G$ in the region of $-18°$ C. to $25°$ C. and these may be considered desirable R groups for some applications.

Figure 1A:
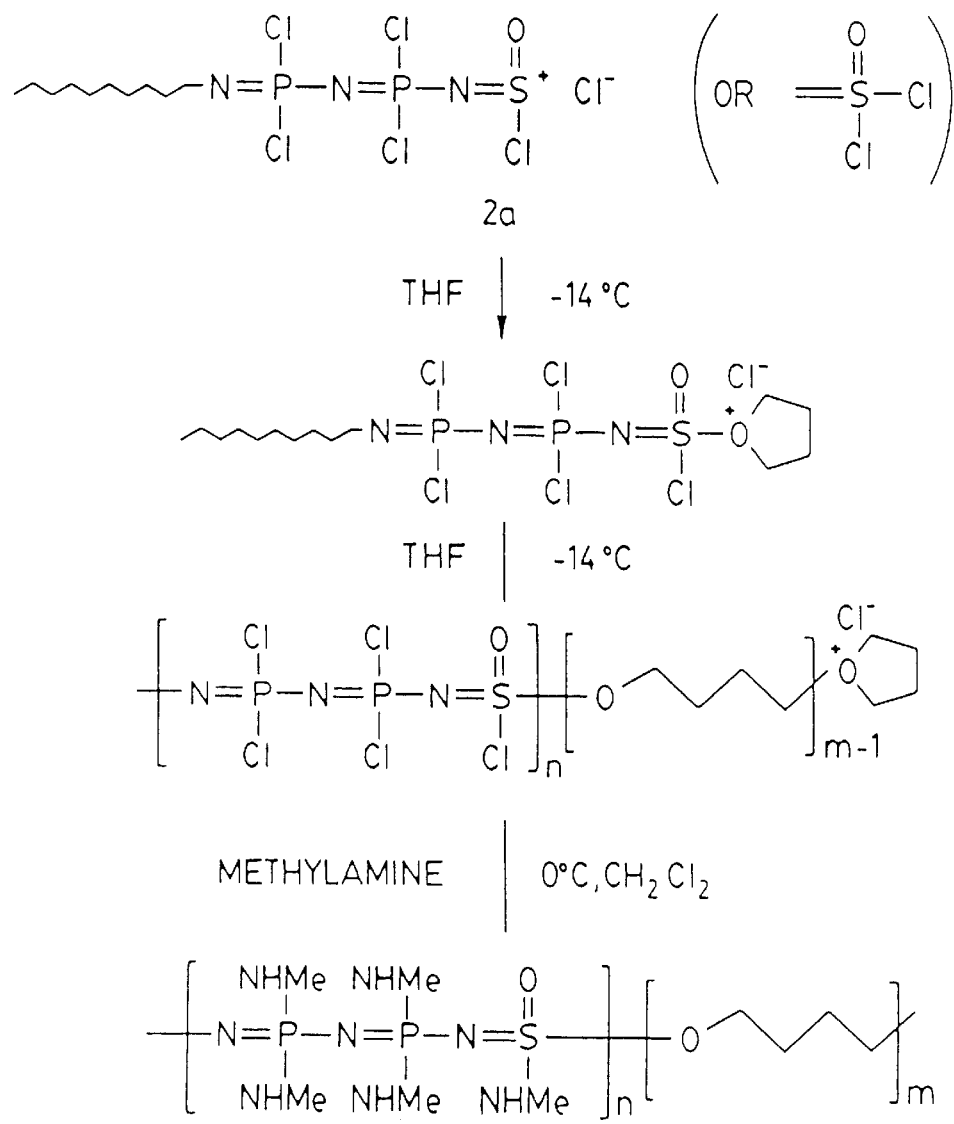
FIG. 1A is a schematic diagram of a polymerization.

Further details of the formation of copolymer 4 can be seen in FIG. 1A and is believed to be representative of one method of forming in general the copolymers of formula B. In this case, the sulfur VI cation from poly (thionylphosphazene) attacks an oxygen site on a THF molecule to form an oxonium ion. Further reaction of this oxonium ion with more monomer generates a poly(THF) block.

In still another of its aspects, the present invention provides a pressure sensor, comprising a stable poll formed from a polymer having a backbone containing nitrogen and one or more of sulfur or phosphorous, the polymer including therein a phosphorescent dye agent, wherein the polymer has a glass transition temperature ranging from −20° C. to 0° C., more preferably −17° C. to 0° C., still more preferably about −17° C.

Preferably, the polymer is hydrolytically stable and more preferably is in the form of sulfur VI.

Thus, the polymers disclosed herein and the polymers formed with these polymers and a dye agent may be useful in a number of environments, including that of pressure sensors, particularly phosphorescent sensors when used with phosphorescent dye agents, in a number of different oxen environments, such as in the earth's atmosphere, in other oxygen-containing fluid environments, such as in gases and liquids containing oxygen, with particular applications including that of measuring the efficiency of aeronautic and aquatic planforms (such as aircraft fuselages and boat hulls), the measurement of the presence of (and possibly the content of) oxygen in ground water and the like.

While discussions herein concern exemplified polymers having nitrogen and both sulfur and phosphorous in the backbone, there are contemplated other polymers which do not necessarily have both sulfur and phosphorous. For example, other polymers may just have repeating S—N—S—N or P—N—P—N backbones, or of other irregularly or regularly repeating combinations of N, S and/or P.

Embodiments of the present invention will be described with reference to the fallowing examples which are presented for illustrative purposes only and are not intended to limit the scope of the inventions.

1. PREPARATION a. Polymer 3

As will be described, poly("butylaminothionylphosphazene) 3 was synthesized by polymerizing a sample of cyclic thionylphosphazene I (2.0 g, 6.1 mmol) in a sealed Pyrex tube at 200° C. for 1 hour according to the technique disclosed by Y. Ni et al (MACROMOLECULES 1992, 27, 7119) to form the polymer 2, namely Polythionylphosphazene at a yield of 1.4 g, at a monomer conversion of 70 percent.

To a stirred solution of polymer 2 (0.7 g 2.1 mmol) in 50 mL of $CH_2Cl_2$ at 0° C. was added slowly n-butylamine (3.1 g, 42 mmol) via syringe. After addition, the reaction was allowed to proceed for 12 hours at room temperature. The solution was concentrated to about one-seventh its volume under vacuum. The polymer 3 was thereafter obtained by drop-wise addition first into water and thereafter into a mixture of methanol and water (1:1 v/v) three times, for removal of residual n-butyl and salt mixtures. Thereafter, the polymer 3 was dried in vacuo to yield 0.71 g of polymer 3 at a monomer conversion of 90 percent. The resulting polymer 3 was a colorless gum and was analyzed using permeation chromatography in tetrahydrofuran with $[Bu_4N]$Br on a WATERS 410 apparatus equipped with a linear ULTRA STYRAGEL column calibrated against monodisperse polystyrene standards. The resulting polymer 3 was found to have monomodal molecular weight distribution of $M_w=1.4\times10^5$ and $M_n=6.7\times10^4$, indicating good polymer properties.

b. Copolymer 4

As will be described, poly("butylaminothionylphosphazene)-b-Poly(tetrahydrofuran) block copolymer 4 was synthesized by carrying out a ring opening polymerization of tetrahydrofuran in the presence of polymer 2.

To the polymer 2 (0.7 g, 2.1 mmol) was added tetrahydrofuran (5 ml 57 mmol) via cannula. Then the resulting solution was transferred to a Pyrex tube via cannula Under nitrogen, the tube was sealed before being kept at −15° C. After approximately two weeks, the solution became very viscous and almost immobile. The gel-like material was then dissolved in tetrahydrofuran (100 mL) for approximately two hours, followed by addition of n-butylamine (3.1 g, 42 mmol) at 0° C. After addition the solution was stirred for 12 hours at room temperature. The solution was concentrated to about one-seventh its original volume under vacuum. The polymer 4 was thereafter obtained by drop-wise addition first into water and then into methanol three times before drying in vacuo to give 1.8 g of polymer 4 with a yield of 95% based on the polymer 4. The resulting material was a colourless gum and was analyzed using permeation chromatography in tetrahydrofuran with $[Bu_4N]$Fr on a Waters 410 apparatus equipped with a linear ULTRASTYRAGL column calibrated It monodisperse polystyrene standards. The resulting polymer material 4 was found to have monomodal molecular weight distribution of $M_w=3.7\times10^5$ and $M_n=1.9\times10^4$.

c. Copolymer 10

Poly(butylaminothionylphosphazene)-b-poly(tetrahydrofuran), (8).

Figure 1B:
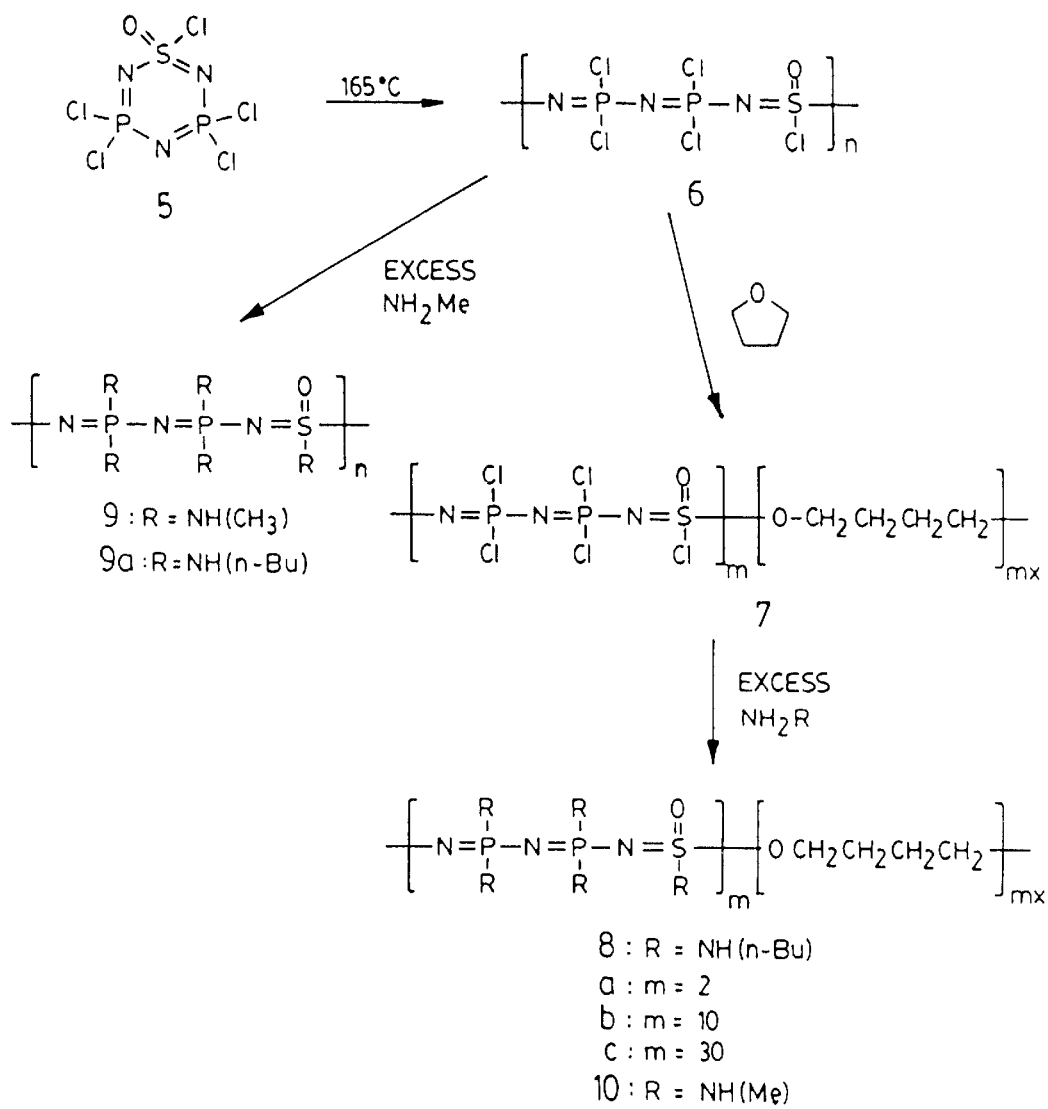
FIG. 1B is a schematic diagram of another polymerization.

Referring to FIG. 1B, the cyclic thionylphosphazene 5 (2.0 g) was heated in an evacuated sealed Pyrex tube at 165° C. for 4 h. The tube contents were then dissolved in ca. 40 ml of CH2Cl2 and the solution was concentrated to ca 10 ml and was the added dropwise to 200 ml of stirred hexanes via cannula. The colorless, moisture sensitive, elastomeric polymer was dissolved in 100 ml of THF and the solution then stored in the refrigerator at −14° C. for 48 h. A significant solution viscosity increase was noticed. n-Butylamine was added drop-wise to the polymer solution which was cooled to 0° C. White precipitation formed immediately after the addition. The solution was concentrated to ca. 20 ml and filtered through a filter frit. The precipitation was carried out by first re-dissolving the dried crude product in Ca. 10 ml of THF then precipitating into water three times followed by precipitating from CH2Cl2 into hexanes three times. Final product was dried from CH2Cl2 under high vacuum for 24 hours at ambient temperature. Yield of 8, a colorless film forming material 1.34 g (84%). 31P NMR (CH2Cl2) d(ppm); 2.05, 1.81. 1H NMR (CDCl3) d(ppm): 3.38 (s, br, THF), 3.04 (m, br, N—H), 2.84 (m, br, butyl), 1.57 (m, br, THF), 1.46 (m, br, butyl), 1.36 (m, br, butyl), 0.91 (m, br, CH3-butyl). 13C NMR (CD2Cl2) d(ppm): 70.9 (—CH2 in poly(THF)), 41.1 (butyl), 34.3 (butyl), 27.0 (CH2 in poly (THF)), 20.7 (butyl), 14.2 (butyl). DSC (° C.), Tg at −70 for (poly(THF)), Tg at −16 for [poly(butylaminothionylphosphazene] block, and Tm at 40 for (poly(THF)). GPC measurement: 8a; Mw=3.05×105, PDI= 1.9; 8b: Mw=2.16×105, PDI=1.5; 8c: Mw=2.36×105, PDI= 1.9. (Note that one can qualitatively control the THF chain length by the time amount of time that the chlorinated polymer is exposed to THF)

Poly(methylaminothionylphosphazene)-b-poly(tetrahydrofuran) (10).

Pure polymer 6 (0.43 g) was dissolved in 20 ml of THF solution and the resulting solution was then stored in the refrigerator at −14° C. for 48 h. A significant solution viscosity increase was noticed. The solution was diluted with 100 ml of CH2Cl2 and pre-dried methylamine gas at 0° C. was bubbled through the solution. White precipitation formed immediately. The reaction mixture became clear after ca 5 minutes. Methylamines was then allowed to bubble through for a further 5 minutes. The solution was warmed to ambient temperature over 2 hours. The solution was concentrated to ca. 20 ml and filtered through a filter frit. The purification was carried out by first re-dissolving the dried crude product in ca. 10 ml of THF then precipitating into water three times followed by precipitating from CH2Cl2 into hexanes three times. Final product was dried from CH2Cl2 under high vacuum for 24 hours at ambient temperature. Yield of 10, a colorless film forming material 0.28 g (89%). 31P NMR (CH2Cl2) d(ppm): 5.10. 1H NMR (CDCl3) d(ppm): 5.51 (m, br SNH), 3.38 (s, br, THF), 3.04 (m, br, PN—H), 2.72 (m, br, CH3), 2.51 (s, br, PNHCH3), 1.57 (m, br, THF), 1.46 (m, br, butyl), 1.36 (m, br, butyl), 0.91 (m, br, CH3-butyl). 13C NMR (CD2Cl2) d(ppm): 70.6 (—CH2 in poly(THF)), 30.3 (SNHCH3), 27.0 (PNHCH3), 26,5 (CH2 in poly(THF)), 14.2 (butyl). DSC (° C.): Tg at −79 for poly(THF) block, Tg at 13 for [poly (methylaminothionylphosphazene)] block, Tm at 34 (poly (THF)). GPC measurement: 10: Mw=1.50×105, PDI=1.9.
Precipitation Experiment to Show that 8 is not a Blend A mixture of 9a (60 mg) and poly(THF) (60 mg) were dissolved in CH2Cl2 (5 ml) and added drop-wise to hexanes (150 ml). The solution was next cooled in an ice bath for 30 min, The resulting white polymer was isolated by decanting off the supernatant and the white polymer was dried in vacuo, resulting in 40 mg of poly(THF). 1H NMR (prior to precipitation) (CDCl3) d(ppm): 3.40 (s, br, THF), 3.04 (m, br, N—H), 2.86 (m, br, butyl), 1.61 (m, br; THF), 1.41 (m, br, butyl), 0.89 (m, br, CH3-butyl), 1H NMR (after precipitation) (CDCl3) d(ppm): 3.41 (s, br, THF), 1.61 (m, br, THF), A sample of 5 was subjected to similar extraction conditions as those described above. 1H NMR of (CDCl3) d(ppm): 3.40 (s, 36.7H THF), 2.92 (m, 2.31H, butyl), 1.61 (m, 40.8, THF), 1.36 (m, 3.2H, butyl), 0.90 (m, 4.4H, butyl). 1H NMR (after precipitation) (CDCl3) d(ppm): 3.40 (s, 35.3H, THF), 2.92 (m, 3.5H, butyl), 1.61 (m, 38.6H, THF), 1.36 (m, 3.7H, butyl), 0.90 (m, 3.91H, butyl).

Characterization

Characterization of Poly(n-butylaminothionylphosphazene)-b-poly(THF) Block Copolymer 8 and 10.

Poly(thionylphosphazenes) are class of inorganic polymers with a backbone of sulfur(VI), nitrogen, and phosphorus atoms. These materials can be regarded as hybrids of poly(oxothiazenes) [S(O)R=N]n and polyphosphazenes [PR2=N]n., Poly(thionylphosphazenes) can be prepared via the ring-opening polymerization (ROP) of the cyclic monomer 5 either thermally at 165° C. or at ambient temperature in solution in the presence of a Lewis Acid initiators such as GaCl3., In a manner analogous to the preparation of hydrolytically stable poly(organophosphazenes) from [NPCl2]n, the hydrolytically sensitive halogenated polymer 6 can be reacted with nucleophilic reagents to afford hydrolytically stable polymers such as 9a. 13.

The ROP mechanism is believed to involve initiation by a cationic intermediate generated via loss of chloride from the sulfur(VI) center followed by propagation steps in which ring-opening of monomer molecules generates a linear polymer with an elertrophilic sulfur(VI) center at the chain end. It was found that dissolving the chlorinated poly (thionylphosphazene) 6 in THF led to an increase in solution viscosity with time. The NMR spectra of the isolated polymer product (7) and materials prepared via replacement of chlorine with alkylamino groups using either butylamine (to afford 8) or methylamine (to afford 10) (FIG. 1B) were consistent with the presence of poly(THF). Subsequent analysis of 7, 8, and 10 indicated that these materials are block copolymers with poly(THF) where the THF polymerization is, we believe initiated by cationic chain ends of 6.

Characterization of 7, 8 and 10 was achieved by 1H, 13C, 31P and Gel Permeation Chromatography (GPC). Significantly, the 31P NMR spectra of 7, 8, and 10 were identical to those of the corresponding homopolymers. This indicated that no reaction with THF to form a graft copolymer had occurred at the phosphorus or sulfur sites in the polymer main chain. Attempts to identify switching groups at the terminal S(VI) centers at the end of the poly (thionylphosphazene) block were, however, unsuccessful. This is a presumably a consequence of the high molecular weights of the materials (by GPC broad essentially monomodal peaks were detected with Mw>105 and PDI values of 1.5–1.9). 1H NMR indicated that qualitative control of the THF block length was possible by varying the reaction time and three polymers with various compositions were prepared, 8a–8c.

The assignment of a block copolymer structure 7, 8, and 10 was also supported by two additional pieces of evidence. Firstly, poly(THF) was precipitated exclusively on addition of a CH2Cl2 solution of a mechanical blend of 1 and polyp(THF) to cold hexanes. FIG. 1 clearly shows the difference in 1H NMR of the sample isolated (i.e. poly(THF) from the experiment and that of the original sample (i.e. the blend). In contrast 1H NMR integration of ratios of the peaks corresponding to the two types of blocks present in 8 did not change under identical precipitation conditions (see FIG. 2). The possibility that material 9 is a simple blend of 1 and poly(THF) was therefore eliminated. A second piece of evidence for block copolymer formation was obtained from the GPC analysis of the methylamino copolymer 10. The methylamino homopolymer 9 possesses a small hydrodynamic radius in THF as this is a poor solvent for this hydrophilic, water-soluble material. Thus artificially low molecular weights are determined by GPC measurements in THF versus polystyrene standards. As expected for the formation of a block copolymer where the new block (poly(THF)) possesses much more favorable segment-solvent interactions, a dramatic increase in apparent molecular weight from Mw=7.0×103 (PDI=1.5) to 1.5×105 (PDI=1.9) was found when comparing the poly[(methylamino) thionylphosphazene] homopolymer (9) and the poly(THF) block copolymer (10) obtained from the same batch of the homopolymer 6.

DSC analysis of 8 and 10 showed thermal transitions for the poly(thionylphosphazene) and poly(THF) blocks. Thus for 8 a Tg at −70° C. and a Tm at 40° C. for the poly(THF) blocks as well as a Tg at −16° C. for the poly(n-butylaminothionylphosphazene) block was detected. For 10, the poly[(methylamino)thionylphosphazene] and poly(THF) blocks also possessed independent thermal transitions (Tg=−79° C. and Tm=34° C. for the poly(THF), Tg=13° C. for the poly[(methylamino)thionylphosphazenes]). The presence of thermal transitions that are similar to those found for the homopolymers indicates that the blocks are incompatible and phase separate in the solid state.

Films of block copolymer 8 are considerably less tacky than those of homopolymer 1 owing to the presence of the reinforcing, crystalline poly(THF) segments and suggested that the materials might possess improved characteristics for pressure sensing applications. An ideal matrix for pressure sensitive composite applications in wind tunnels, for examples also requires a Tg lower than the working temperature of the experiment (which can be as low as −10° C.). The Tg of the methylamino analog 10 was found to be 13° C. making it less suitable for pressure sensitive paint applications compared to 8 (Tg=−17° C.) and so only the latter material was investigated,

2. PREPARATION OF COATINGS

Commercial grade Platinum Octaethylporphyrin (hereinafter referred to as 'PtOEP') was obtained from PORPHYRIN PRODUCTS, INC. and was used without further purification. At 10 ppm dye agent concentrations, PtOEP has the following luminescent characteristics: $\lambda_{ox}$=380 nm, $\lambda_{om}$=645 nm, $\tau$=79 $\mu$s.

[Ru(4,7-diphenylphen)$_3$]Cl$_2$ (hereinafter referred to as 'RuPHEN') was synthesized according to the procedure described by Lin et al, in ANALYST 1993, 118,289. At 100 ppm dye agent concentrations, RuPHEN has the following luminescent characteristics: $\lambda_{ox}$=450 nm, $\lambda_{om}$=610 nm, $\tau$=6.9 $\mu$s.

RuPHEN has the advantage that excitation occurs by light with a longer wavelength than the wavelength of the light used for PtOEP, thereby reducing dye agent photo decomposition and allowing for the use of more convenient photo illumination sources.

Both the PtOEP and RuPHEN were incorporated into both the polymer 3 and the copolymer 4 by way of a solvent mixture to form a precursor for a number of polymer coatings. The solvent mixture was formed with 1,1,1-Trichloroethane as a solvent at room temperature. Alternative solvents include methylene chloride, methanol or ethanol, also at room temperature.

The solvent mixtures containing the dye agent and the polymer 3 were spray coated onto the surface of interest using both stainless steel and alumina substrates. The selected data described below is derived from samples all of which used a stainless steel substrate. Following standard instructions, selected surfaces were pre-coated with an epoxy primer of a two part system which consisted of Super-One Coat (trademark) White D3400 and Glass Activator D3498 available from PRATT AND LAMBERT.

The dye agent concentration in the resulting polymer matrices ranged from 10 ppm to 1000 ppm and this was measured knowing the volume percent of the dye agent in the solvent mixture.

The composite films varied in thickness between 5 and 15 micrometers. This thickness was estimated by weighing the substrate before and after applying the film and calculating the thickness based on the approximate known density of the polymer.

Solvent mixtures were prepared containing PtOEP and polymer 3 with a dye agent concentration of 1000 ppm The solvent mixture was applied to several substrates including stainless steel and alumina. Selected samples were pre-coated with an epoxy primer to enhance reflection and therefore increase the intensity of the analyzed light.

3. ANALYSIS

Figure 9:
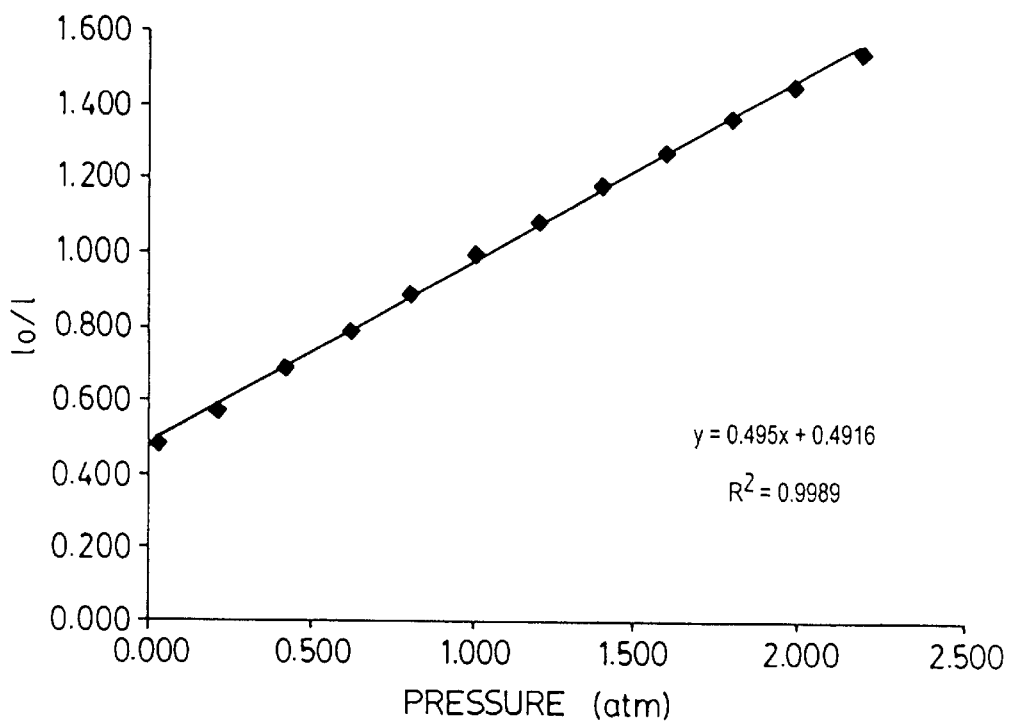
FIG. 9 is a plot of a Luminescence Intensity Ratio versus pressure for still another exemplified polymer.

Samples were placed in a pressure chamber which was equipped with a viewing window to permit in-situ pressure measurements. The pressure chamber was equipped with an adjustable pressure supply, itself having alternative gas sources, namely oxygen and nitrogen, allowing the content of the chamber to be changed as will be described below. All the measurements were made at room temperature (25±1° C.), Response times of the sensing films were measured by switching the gas supply alternatively between air and nitrogen, An Ar+ ion laser (MODEL 3000, LEXEL LASER, INC.) and a Kr+ ion laser (MODEL 3500, LEXEL LASER, INC.) were used, being tuned at 476.5 and 530.87 nm respectively. Xenon strobe light source (MODEL MVCS-2200, BG&G ELECTRO-OPTICS) was also used, being operated at 80 Hz with a 40 nm band pass filter centered at 400 nm. The laser beam was expanded by a light shaping diffuser to project a uniform illumination on samples. Two cut-off filters (RG 610 nm for PtOEP, OG 590 nm for RuPHEN were placed in font of a liquid nitrogen cooled CCD detector (MODEL LN/CCD, PRINCETON INSTRUMENTS, INC.) with 578×384 pixels in a cell size of 13.25×8.83 min. Luminescent light from the sample surface was collected with a camera lens (NIKON, 55 mm, 1:1.2) and imaged onto the CCD detector. The pressure of the sample chamber was measured by a pressure gauge (MODEL FA233, WALLACE AND TIERNAN) with an accuracy of ±0.1 psi, Other experiments carried out on copolymers 8, 9 and 10, indicate that the homopolymer 1 provides a promising matrix for phosphorescent sensing composites. As the copolymer 8 forms relatively high quality, free standing films, use of such films were explored for sensing composites. Phosphorescent composites were generated us the phosphorescent dye agent [Ru(4,7-diphenylphen)3]Cl2 dye agent (lex=450 nm, lem=610 nm, t=6.9 ms at 10 ppm agent concentration in solution).9 Films of polymer 8 were solution cast onto aluminum slides which were previously covered with a white primer paint to increase the intrinsic intensity of the detected light. The slides were then placed in a chamber containing air whose pressure was varied incrementally from ca, 0.30 to 33.00 psi, and the Tumescence intensity (I) was measured. The performance of the material was evaluated from the sensitivity (S) and the linearity of Stern-Volmer plot, 11.0/I=A+S(P/P1.0) (see FIG. 9). All Stern-Volmer plots were substantially linear giving R2 in the range of 0.989–0.999.

The concentration of the dispersed dye agent in the composite was also investigated in order to maximize the sensitivity of the material. Results of these tests using a range of [Ru(Ph2phen)3]Cl2 concentrations from 500 to 2500 ppm are shown in Table 5 and suggest that sensitivity of the material is not dependent on the dye agent concentration over the range. There was no significant decrease in sensitivity of the material, which would have indicated self-quenching by the dye agent molecules at high concentration. This may point to the compatibility of the dye agent and the polymer 8 which leads to a homogenous dispersion rather that dye agent aggregation, a problem that has been noted in silicone-based systems.

The photo stability of the material, 8, was examined by collecting data points after five different time intervals while exposing the material to UV light (1=450 nm, intensity=0.17 mW/cm2 at the samples). The data shows the intensities measured over a 2 hour interval shows no significant deviation (see Table 6). To verify that the material does not degrade significantly, the sensitivity, of 8 was examine over a 4 hour period. This experiment clearly indicates that the material does not photo decompose as seen by both the sensitivities which are the same within error and the Stern-Volmer plots were all linear as seen in the R2 values which were 0.998 or better (Table 7), that is between 0.998 and 1.0.

The influence on the length of the poly(THF) block on the sensitivity of the matrices indicated that for thionylphosphazene: poly(THF) block length ratios of c.a, 1:2 an increase in sensitivity is detected. As the degree of crystallinity of the overall copolymer is presumably increased by virtue of increasing length of the poly(THF) blocks, the permeability decreases and hence sensitivity is lower for longer block lengths (Table 4). The importance of using the copolymer 8 rather than mechanical blends of poly(n-butylaminothionylphosphazene) and poly(THF) was evident from a comparative series of experiments on the two types of materials (see Table 9). These experiments showed that the sensitivity of the blends with THF (0.281–0.304) was significantly less that of the homopolymer 1 (0.519) whereas the sensitivity of the block copolymers 8 (0.470–0.556) was greater.

Thus, the ease with which fee standing films of poly (aminothionylphosphazenes)-b-poly(tetrahydrofuran) can be cast without the use of a curing agent in addition to the photophysical stability of the materials is promising. As a consequence of their material advantages, well-defined Stern-Volmer behavior and improved compatibility with the dye agents, poly(aminothionylphosphazenes)-b-poly (tetrahydrofuran) materials appear promising candidates as matrices for pressure sensing applications.

4. RESULTS: PtOEP COATINGS a. PtOEP-Containing Polymer 3 Coatings Without Primer

FIG. 1 shows the behaviour of PtOEP in a matrix of polymer 3 in the absence of primer coatings with an air pressure change from 0.01 atm, to 2.38 atm. In this case, the dye agent concentration was 1000 ppm, At 1.0 the LIR was about 58. At 2.38 atm, the luminescence intensity was only about 1/125th the luminescence intensity at 0.01 atm, indicating that the polymer 3 has significant oxygen permeability. The Stern Volmer equation was used to fit the intensity data, giving the variables A=0.0470 and B=0.0950 with a correlation coefficient $R^2$=0.9982 indicating a relatively fine and substantially even distribution of phosphorescent sites across the coating and thus indicating that the polymer matrix was compatible with PtOEP without significant microheterogenieties.

b. PtOEP-Containing Polymer 3 Coatings With Primer

Figure 2:
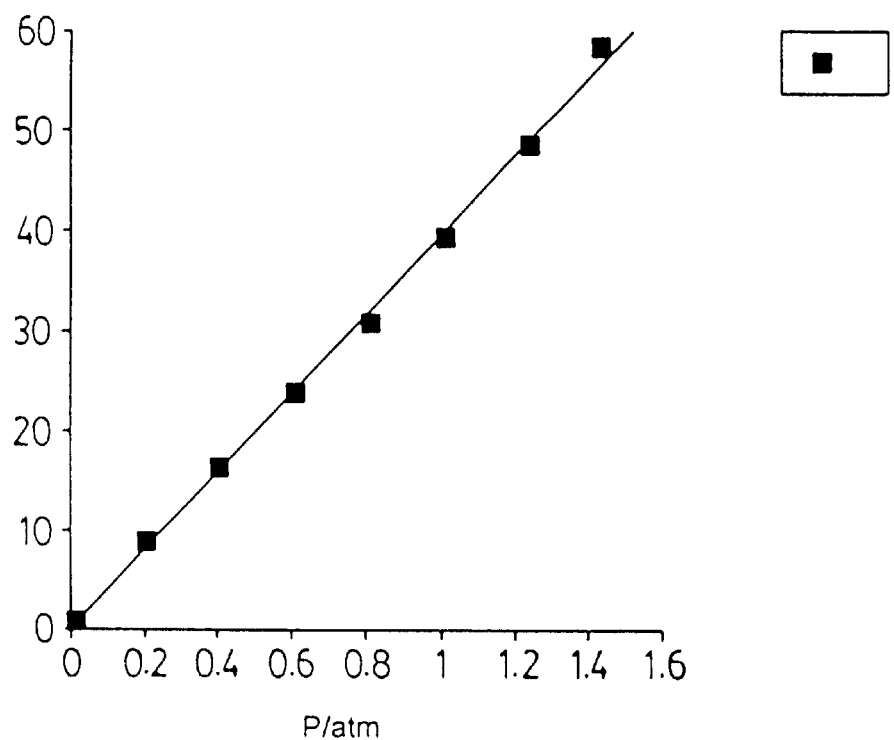
FIG. 2 is a plot of a Luminescence Intensity Ratio versus pressure for another exemplified polymer.

FIG. 2 shows the behaviour of PtOEP in a matrix of polymer 3 with primer coatings and with an air pressure change from 0.01 atm, to 1.6 atm. In this case, the dye agent concentration was 1000 ppm. At 1.6 atm, the luminescence intensity was only about 1/58th the luminescence intensity at 0.01 atm, indicating again that the polymer 3 has significant oxygen permeability. Using Stern-Volmer, the best fit for one such system gave A 0.0226 and B a 0.9498 with a correlation coefficient $R^2$=0.997 indicating a steeper slope in view of the use of the primer coating.

c. PtOEP-Containing Copolymer 4 Coatings Without Primer

Figure 3:
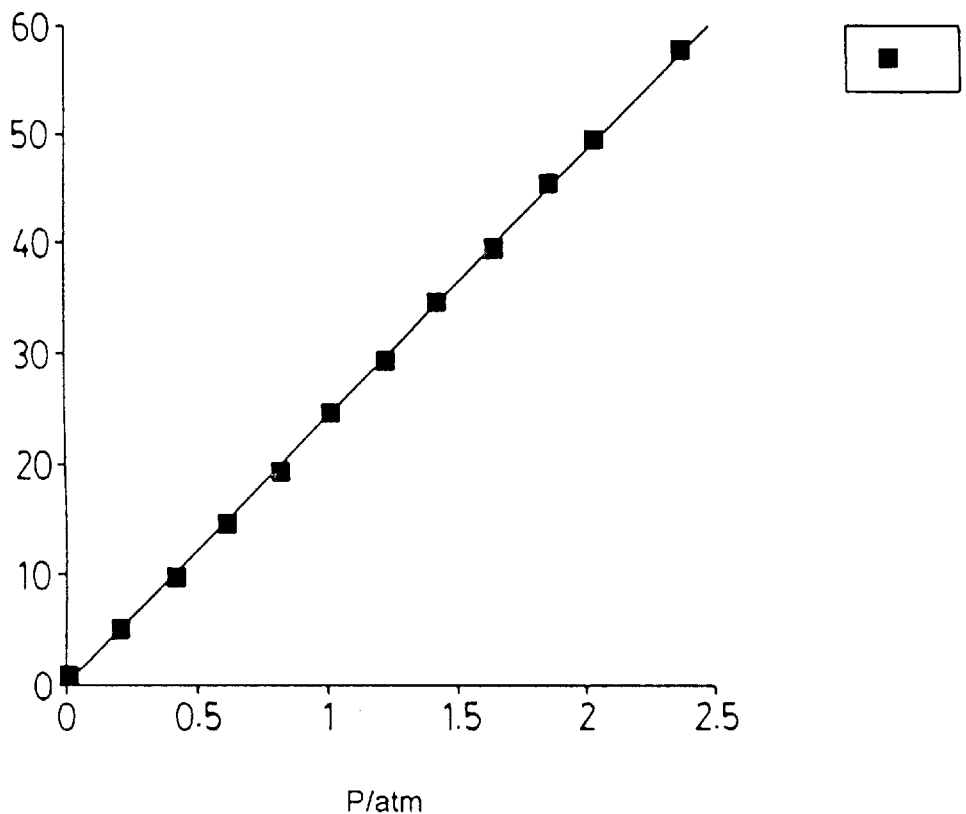
FIG. 3 is a plot of a Luminescence Intensity Ratio versus pressure for still another exemplified polymer.

FIG. 3 shows the behaviour of PtOEP in a matrix of the copolymer 4 in the absence of primer coatings with an air pressure change from 0.01 atm, to 2.38 atm. In this case, the dye agent concentration was 1000 ppm. At 1.0 atm, the LIR $I_{0.00}/I_{1.00}$ was about 18, indicating that the copolymer 4 also has significant oxygen permeability.

The Stern Volmer equation was used to fit the intensity data, giving the variables A=0.0470 and B=0.0950 with a correlation coefficient R=0.9995 indicating an even and fine distribution of phosphorescent sites across the coating and thus indicating that the copolymer 4 was compatible with PtOEP without significant microheterogenieties.

d. PtOEP-Containing Copolymer 4 Coatings With Primer

Figure 4:
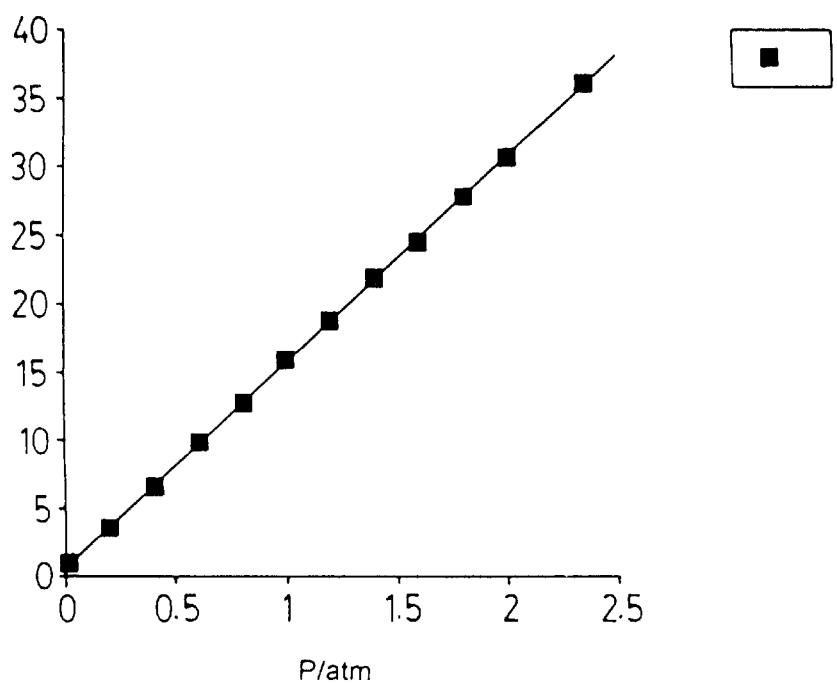
FIG. 4 is a plot of a Luminescence Intensity Ratio versus pressure for still another exemplified polymer.

FIG. 4 shows the behaviour of PtOEP in a matrix of copolymer 4 with primer coatings with an air pressure change from 0.01 atm, to 2.38 atm. In this case, the dye agent concentration was 1000 ppm. The luminescence intensity was shown to decrease sharply with the increase of air pressure. At 0.2 atm, the intensity of luminescence emission was 3.5 times less than that of luminescence emission at 0.00 atm. From 0.2 to 1.0 atm, the intensity of luminescence emission decreased again by more than 4-fold. From 0.00 to 1.0 atm the LIR $I_{0.00}/I_{1.00}$ was approximately 16. The relatively steeper slope is evident due to the use of the polymer 3.

e. Polymer 3 Versus Silicone Coatings Using PtOEP

Most known PtOEP based systems in cross-linked silicone polymer matrices with similar dye agent concentrations show the value of $I_{0.00}/I_{1.00}$ less than 10. Most of those systems have non-linear dependence on air pressure which is characteristic of different quenching environments and less predictable behaviour. PtOEP based polymer 3 was compared against other PtOEP based polysiloxane polymers, in this case GE RTV-118 siloxane polymer matrix available from GENERAL ELECTRIC. Coated samples were formed, each without a primer pre-coat and each using 100 mg of polymer resulting in a thickness about ten times that of the PtOEP based polymer 3 and copolymer 4 described above.

Under the same measurement conditions with substantially the same dye agent concentration, the polysiloxane polymer coatings failed to give any detectable signal. It is concluded therefore, that PtOEP based polysiloxane systems without primer give much lower absolute intensity compared with PtOEP-based polymer 3 and copolymer coatings described above.

5. RESULTS RuPHEN COATINGS a. RuPHEN/Poly 3 Coatings

Figure 5:
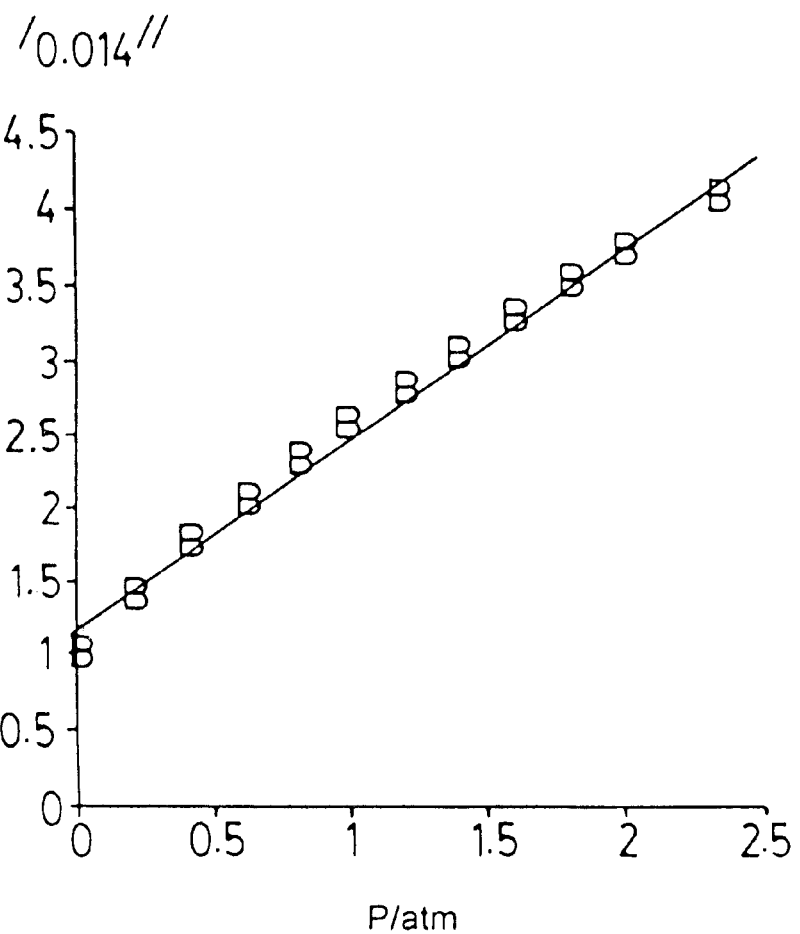
FIG. 5 is a plot of a Luminescence Intensity Ratio versus pressure for still another exemplified polymer.

A solvent mixture was formed as above in the polymer 3, in is case with a RuPHEN dye agent concentration of 500 ppm. The solvent mixture was applied to a surface without a primer coating. FIG. 5 shows the behaviour of RuPHEN in a matrix of polymer 3 in the absence of primer coatings with an air pressure change from 0.01 atm, to 2.38 atm. The coating exhibits almost linear pressure dependence.

b. Polymer 3 Versus Silicone Coatings Using RuPHEN

In comparison under similar conditions, the RuPHEN based RTV 118 silicone system (at a dye agent concentration of 500 ppm) gave a downward curve over the range from 0.01 atm to 2.38 atm with $I_{0.00}/I_{1.00}=4.36$. Although the RuPHEN based polymer 3 was slightly less sensitive to pressure ($I_{0.00}/I_{1.00}=2.55$), the RuPHEN based polymer 3 had less microheterogeneity and the luminescence data fit the Stern Volmer model with a correlation coefficient of 0.991 and gave values of A=0.998 and B=0.4997.

c. Copolymer 4 Versus Silicone Coatings Using RuPHEN

Figure 6:
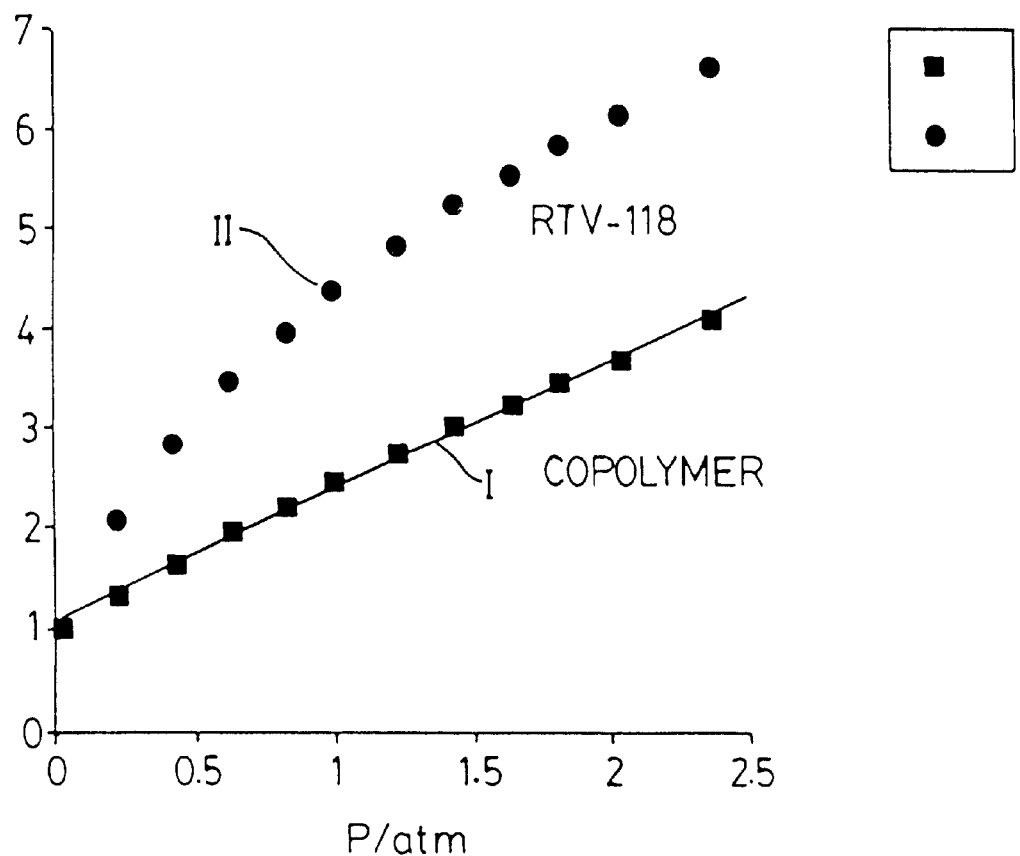
FIG. 6 is a comparative plot of a Luminescence Intensity Ratio versus pressure for still another exemplified polymer against a conventional material.
Figure 7:
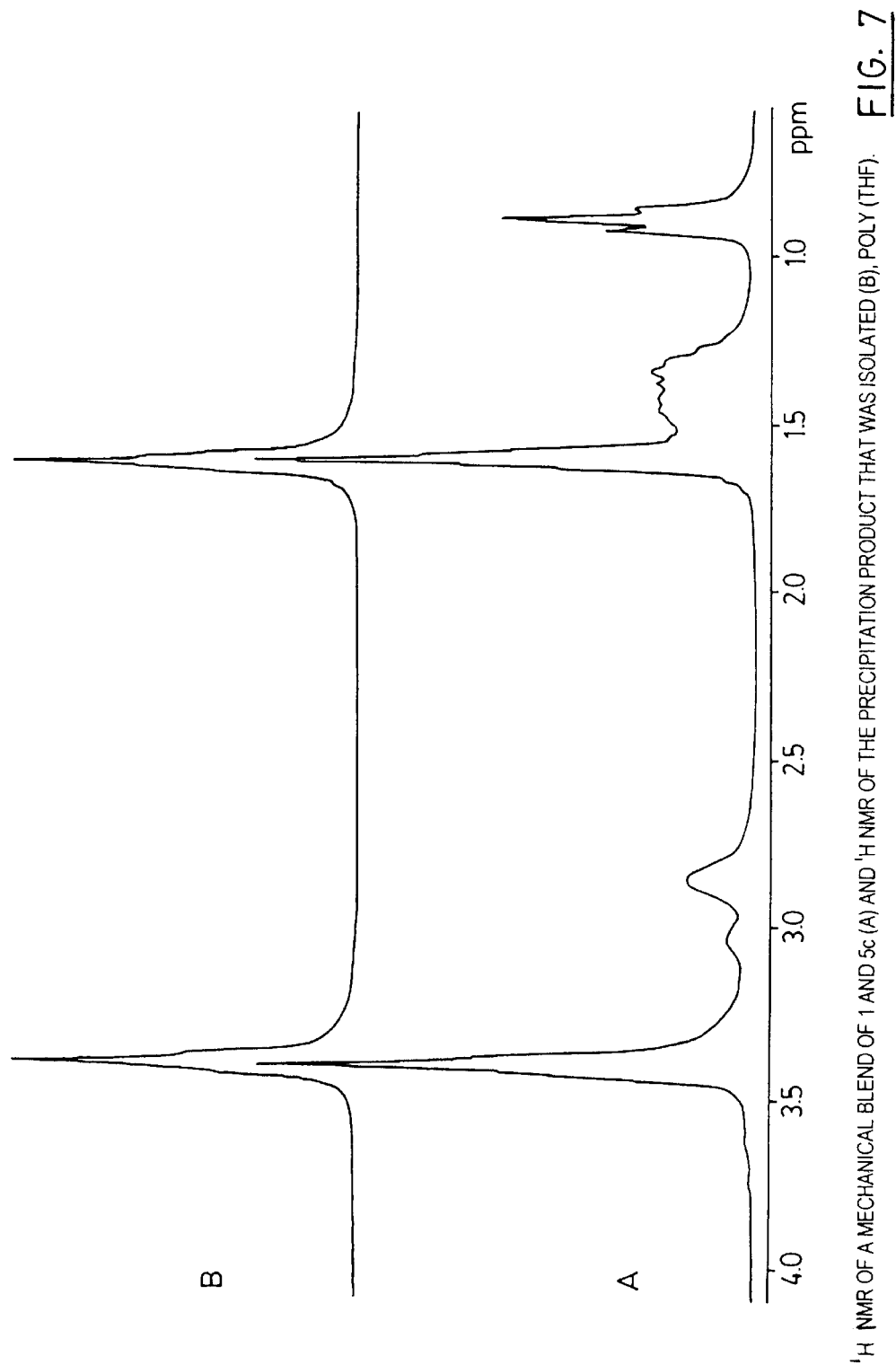
FIG. 7 is an HNMR spectral plot of several exemplified polymers.
Figure 8:
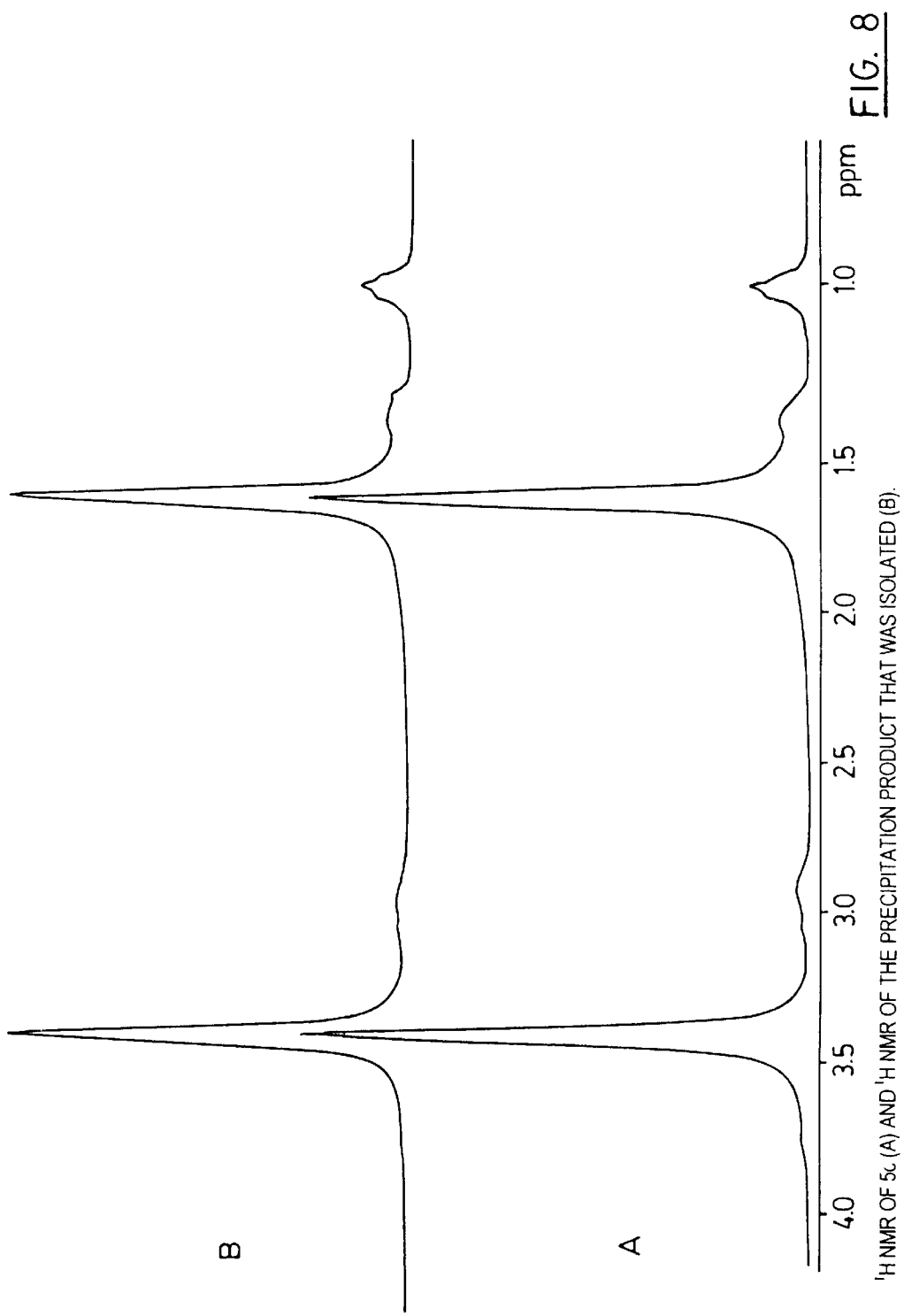
FIG. 8 is another HNMR spectral plot of several other exemplified polymers.

As mentioned earlier for PtOEP, most known RuPHEN-based systems in cross-linked silicone polymer matrices with si dye agent concentrations show the value of $I_{0.00}/I_{1.00}$ less than 10. Most of those systems have non-linear dependence on air pressure which is characteristic of different quenching environments and less predictable behaviour. FIG. 6 is a comparative plot of a RuPHEN based copolymer 4 coating shown by a curve of solid rectangles at 'I' and a RuPHEN based RTV-118 silicone polymer coating shown by a curve of solid circles at 'II'. Using Stern-Volmer, the best fit for the system of curve 'I' gave A=1.08 and B=1.29 with a correlation coefficient $R^2=0.997$. In contrast, the curve 'II' shows the traditional flattening curve representative of conventional silicone systems in the higher LIR/Pressure ranges.

Each of the following references are incorporated herein by reference:

1. a) T. M. Swager, M. J. Marsella, Ady. Mater. 1994, 6.595. b) Q. Thou. T. M. Swager, 1. Am. Chem. Soc. 1995. 117.7017. c) *Fluorescent Chemosensors for Ion and Molecular Recognition* (Ed: A. W. Czarnik), ACS Symposium Series 538. American Chemical Society, Washington, D.C. 1993. d) P. Bauerle S. Scheib, *Adv. Mater.* 1993,5.848. e) P. N. Barlett, P. R. Birkin, *Synth. Met.* 1993, 61,15.
2. Chemical. Biochenical, and Environmental Sensors (Eds: R. A. Liebman, M. T. Wlodarczyk), The International Society for Optical Engineering, Bellinham, Wash. 1989. Vol. 1172.
3. R. Dorn, D. Baums, P. Kersten, R. Regener, *Adv. Mate.* 1992,4,464.
4. X. M. Li, P. C. Ruan, W Y. Wong, Analyst 1993, 118, 289.
5. a) C. Prelninger, I. Klimant, O. S. Wolfbeis, *Anal. Chem.* 1994,66.1841. b) G. Di Marco, M. Lanza, S. Campagna, *Adv. Mater.* 1995, 7, 468. c) I. Kilmant, O. Woilbeis, *Anal. Chem.* 1995, 67, 3160. d) M. C. Moreno Bondi, O. S. Woilbeis, M. J. P, Leiner, B. P. H. Schaffar, *Anal Chem.* 1990, 62, 2377.
6. J Kavandi, J Callis. M. Gouterman, G. Khalil, D. Wright, E. Green, D. Burns, B. McLachlan, *Rev. Sci. Instrum.* 1990,61,3341.
7. a) J. R. Bacon, J. N. Demas, *Anal. Chem.* 1987,59, 2780. b) J. N. Demas. B. A. De Graff, *Anal. Chem.* 1991, 63, 829A.
8. B. R. Carraway, J. N. Demas, B. A DeGraff, J. R. Bacon, *Anal. Chem.* 1991,63, 337.
9. Z. Pang, X. Gu, A. Yeka, Z. Masoumi, J. B. Coil, M. A. Winnik, I. Manners, *Adv. Mat* 1996, 8,768.
10. A. Yekta, Z. Masoumi, M. A, *Can. J. Chem.* 1995,73, 2021,
11. a) J. A. Dodge, I. Manners, G. Renner. H. R. Allcock, O. Nuyken, *J. Am. Chem. Soc.* 1993,26, 11. b) H. R. Allcock, J. A, Dodge, I. Manners, *Macromolecules* 1993,26, 11.
12. H. R. Allcock, R. L Kugel, *J. Am. Chem. Soc.* 1965, 87,4216.
13. Y Ni P, Park, M. Liang, 3. Massey, C. Waddling, I. Manners, *Macromolecules* 1996,29, 3401.
14. D. P. Gates, M. Edwards, L. M. Liable-Sands, A. L. Rheingold, I. Manners, *J. Am. Chem. Soc.* 1998,120 (13), 3249.
15. a) I. Manners, *Coor. Chem. Rev.* 1994, 137, 109. b) M. Liang, C. Wadding, C. Honeyman, D. Foucher and I. Manners, *Phosphorus Sulfur Silicon Relat. Elem.* 1992, 64, 113,
16. P. Dreyfuss, *Poly(tetrahydrofuran)*; Gordon and Breach Science Publishers: New York, 1982.
17. y Ni, A. Stammer, M. Liang, 3. Massey, G. 3. Vaneso, I. Manners, *Macromolecules* 1992,25, 7119.

FORMULA A

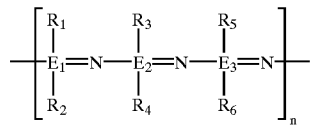

FORMULA B

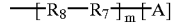

1

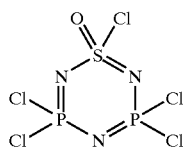

2

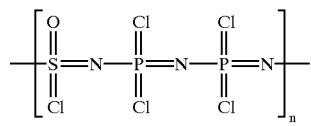

3

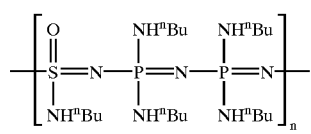

4

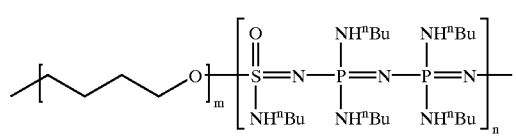

TABLE 1

Selected characterization data for poly(thionylphosphazenes) and halogen or aryloxy side groups.

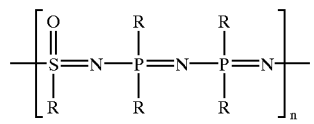

| | | | GPC[a] | | 31P NMR[b] | $T_g$ |
|---|---|---|---|---|---|---|
| STRUCTURE | R' | R | $\overline{M}_w$ | $\overline{M}_n$ | (ppm) | (° C.) |
| 16 | Cl | Cl | — | — | −10.0[c] | −46 |
| 18 | F | Cl | — | — | −8.6[c] | −56 |
| 19 | Cl | OPh | $5.8 \times 10^4$ | $4.0 \times 10^4$ | −21.5 | 10 |
| 19 | Cl | $OC_6H_4Ph$-p | $1.4 \times 10^5$ | $5.1 \times 10^4$ | −20.9 | 55 |
| 19 | Cl | $OC_6H_4CMe_2Ph$-p | $1.1 \times 10^5$ | $6.3 \times 10^4$ | −21.0 | 43 |
| 19 | Cl | $OC_6H_4Bu^t$-p | $4.3 \times 10^4$ | $3.7 \times 10^4$ | −21.0 | 42 |
| 19 | Cl | $OC_6H_4CF_3$-m | $1.8 \times 10^5$ | $1.5 \times 10^5$ | −21.0 | −25 |
| 19 | Cl | $OC_6H_4CF_3$-p | $7.4 \times 10^4$ | $5.5 \times 10^4$ | −21.5 | 18 |
| 20 | F | OPh | $3.8 \times 10^4$ | $2.5 \times 10^4$ | −20.3 | −15 |
| 20 | F | $OC_6H_4Ph$-p | $9.0 \times 10^4$ | $5.8 \times 10^4$ | −19.5 | 48 |

[a]in THF using polystyrene standards;
[b]in THF; [c]in $CH_2Cl_2$

TABLE 2

Selected characterization data for poly[(amino)thionylphosphazenes] and poly(thionylphosphazenes) with alkoxy substituents.

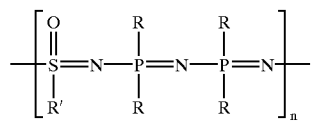

| | | | GPC[a] | | 31P NMR[b] | $T_g$ |
|---|---|---|---|---|---|---|
| STRUCTURE | R' | R | $\overline{M}_w$ | $\overline{M}_n$ | (ppm) | (° C.) |
| 21 | 10% Cl 90% NHMe | NHMe | — | — | 5.0 (br) | — |
| 21 | 50% Cl 50% $NHBu^n$ | $NHBu^n$ | $1.4 \times 10^5$ | $6.7 \times 10^4$ | 2.1, 2.4 | −17 |
| 21 | 50% Cl 50% $NHCH_2CH=CH_2$ | $NHCH_2CH=CH_2$ | $7.1 \times 10^4$ | $2.9 \times 10^4$ | 0.1, 0.2 | −40 |
| 21 | 20% Cl 80% $NHC_6H_5$ | $NHC_6H_5$ | $1.3 \times 10^5$ | $7.4 \times 10^4$ | −18.6 | 101 |
| 23 | Cl | 40% $OCH_2CF_3$ 60% $OC_6H_4Ph$-p | $1.2 \times 10^5$ | $7.7 \times 10^4$ | −14 (br) −17 (br) −21 | 25 |
| 23 | Cl | 25% $OBu^n$ 75% $OC_6H_4CF_3$-m | $1.3 \times 10^5$ | $9.5 \times 10^4$ | −19.7 (br) −21.6 | −14 |
| 23 | Cl | 25% $OCH_2CH=CH_2$ 75% $OC_6H_4CF_3$-m | $7.9 \times 10^4$ | $4.6 \times 10^4$ | −19.0 (br) −19.5 (br) −21.5 | −18 |

[a]in THF using polystyrene standards;
[b]in THF.

SCHEME I

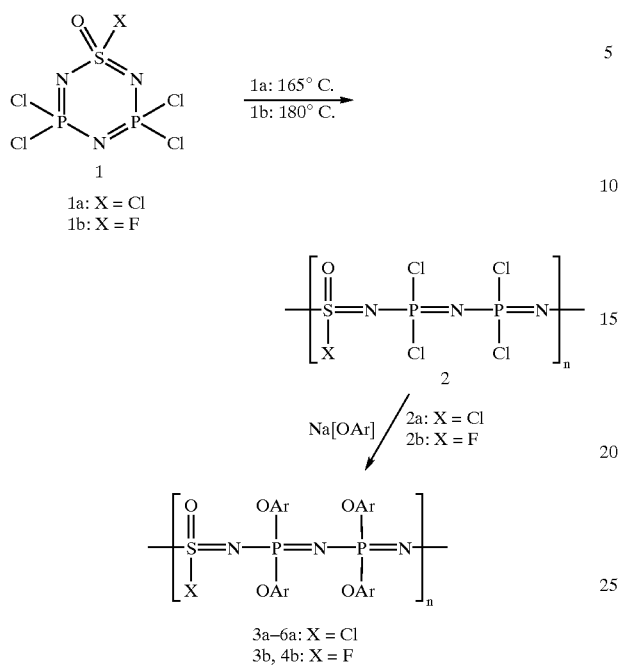

3a–6a: X = Cl
3b, 4b: X = F

TABLE 3

| | X | OAr |
|---|---|---|
| 3a | Cl | —O—C₆H₅ (phenoxy) |
| 4a | Cl | —O—C₆H₄—C₆H₅ (biphenyloxy) |
| 5a | Cl | —O—C₆H₄—C(CH₃)₂—C₆H₅ |
| 6a | Cl | —O—C₆H₄—CF₃ (meta) |
| 3b | F | —O—C₆H₅ |
| 4b | F | —O—C₆H₄—C₆H₅ |

TABLE 4

ANALYTICAL AND GLASS TRANSITION DATA FOR POLYMERS 2a–6a and 2b–4b

| POLYMERS | GPC $M_w$, $M_n$ | elem. anal. calc/found | | $T_g$, °C |
|---|---|---|---|---|
| 2a | | | | −46 |
| 2b | | | | −56 |
| 3a | $5.8 \times 10^4$, $4.0 \times 10^4$ | C | 51.48/51.70 | 10 |
| | | H | 3.60/3.61 | |
| | | N | 7.50/7.46 | |
| | | Cl | 6.33/5.68 | |
| 4a | $1.4 \times 10^5$, $5.1 \times 10^4$ | C | 66.70/66.38 | 55 |
| | | H | 4.20/4.28 | |
| | | N | 4.86/4.80 | |
| | | Cl | 4.10/3.78 | |
| 5a | $1.1 \times 10^5$, $6.3 \times 10^4$ | C | 69.80/67.47 | 43 |
| | | H | 5.86/4.79 | |
| | | N | 4.07/3.56 | |
| | | Cl | 3.43/3.78 | |
| 6a | $1.8 \times 10^5$, $1.5 \times 10^5$ | C | 40.43/40.28 | −25 |
| | | H | 1.94/2.03 | |
| | | N | 5.05/5.00 | |
| | | Cl | 4.26/5.09 | |
| 3b | $3.8 \times 10^4$, $2.5 \times 10^4$ | C | 53.04/52.77 | −15 |
| | | H | 3.70/3.77 | |
| | | N | 7.73/7.66 | |
| | | F | 3.49/3.49 | |
| 4b | $9.0 \times 10^4$, $5.8 \times 10^4$ | C | 68.00/67.40 | 48 |
| | | H | 3.81/4.48 | |
| | | N | 4.96/4.99 | |

TABLE 5

SENSITIVITY OF BLOCK COPOLYMER 5c AS A FUNCTION OF Ru DYE CONCENTRATION.

| DYE CONC. (ppm) | S |
|---|---|
| 500 | 0.486 ± 0.033 |
| 1000 | 0.495 ± 0.029 |
| 1500 | 0.494 ± 0.026 |
| 2000 | 0.488 ± 0.031 |
| 2500 | 0.482 ± 0.034 |

TABLE 6

INTENSITY OF BLOCK COPOLYMER 5c AT 1 ATM OVER A 2 HOUR INTERVAL.

| TIME (MIN.) | I (AT 1 ATM) |
|---|---|
| 0 | 1838 ± 56 |
| 60 | 1616 ± 56 |
| 75 | 1591 ± 52 |
| 90 | 1574 ± 52 |
| 120 | 1525 ± 51 |

TABLE 7

SENSITIVITY OF BLOCK COPOLYMER 5c AS A FUNCTION TIME.

| TIME (HOURS) | S |
|---|---|
| 0 | 0.491 ± 0.033 |
| 3 | 0.488 ± 0.027 |
| 4 | 0.488 ± 0.024 |

TABLE 8

SENSITIVITY OF $(PTP)_{TM}$-B-POLY $(THF)_{TTLX}$ COPOLYMER 5 AND HOMOPOLYMER AS A FUNCTION OF THF CHAIN LENGTH

| X | Mw (PDI) | S |
|---|---|---|
| 0, (1) | $3.69 \times 10^5$ (1.8) | $0.519 \pm 0.031$ |
| 2, (5a) | $3.05 \times 10^5$ (1.9) | $0.556 \pm 0.029$ |
| 10, (5b) | $2.61 \times 10^5$ (1.5) | $0.470 \pm 0.031$ |
| 30, (5c) | $2.38 \times 10^5$ (1.9) | $0.495 \pm 0.033$[a] |

[a] THE STANDARD DEVIATION IN 6 SEPARATE EXPERIMENTS OF THIS SAMPLE WAS FOUND TO BE $0.495 \pm 0.007$.

TABLE 9

SENSITIVITY OF THE POLY (AMINOTHIONYLPHOSPHAZENE) 1/POLY (THF) BLENDS AS A FUNCTION OF RELATIVE COMPOSITION.

| % PTP[a] | % POLY (THF)[b] | S |
|---|---|---|
| 100 | 0 | $0.519 \pm 0.039$ |
| 75 | 25 | $0.284 \pm 0.038$ |
| 50 | 50 | $0.281 \pm 0.031$ |
| 25 | 75 | $0.304 \pm 0.032$ |
| 0 | 100 | $0.374 \pm 0.029$ |

[a] $Mx = 3.69 \times 10^5$, PDI = 1.8
[b] $Mw = 8.14 \times 10^4$, PDI = 1.6

What is claimed is:

1. A pressure sensor comprising a polymeric material having a backbone containing nitrogen and either sulfur or phosphorous or combinations thereof, the polymeric material having a phosphorescent dye agent distributed therein in sufficient concentration to detect changes in pressure, wherein said polymeric material has a glass transition temperature ranging from −20° C. to 0° C.

2. A pressure sensor as defined in claim 1 wherein said polymeric material has a glass transition temperature ranging from −17° C. to 0° C.

3. A pressure sensor as defined in claim 2 wherein said polymeric material has a glass transition temperature of about −17° C.

4. A pressure sensor as defined in claim 1 further comprising a substrate having a surface, with said polymer material having said phosphorescent dye agent distributed therein formed as a coating thereon.

5. A pressure sensor comprising a polymeric material having a backbone containing nitrogen and either sulfur or phosphorous or a combination thereof, the polymeric material having a phosphorescent dye agent distributed therein to detect partial pressure of oxygen and wherein the sensor is operatively characterized by a Stern Volmer plot having a linearity ranging from 0.985 to 1.0.

6. A pressure sensor as defined in claim 5 wherein said sensor is operatively characterized by a Stern Volmer plot having a linearity ranging from 0.985 to 0.995.

7. A pressure sensor as defined in claim 6 wherein said sensor is operatively characterized by a Stern Volmer plot having a linearity ranging from 0.990 to 0.995.

8. A pressure sensor as defined in claim 5 wherein said sensor is operatively characterized by a Stern Volmer plot having a linearity ranging from 0.996 to 0.999.

9. A pressure sensor as defined in claim 5 wherein the dye is present at a dye concentration ranging from 1 ppm to 3000 ppm.

10. A pressure sensor as defined in claim 9 wherein the dye concentration ranges from 750 to 2000 ppm.

11. A pressure sensor as defined in claim 10 wherein the dye concentration ranges from 1000 to 1500 ppm.

12. A pressure sensor as defined in claim 11 further comprising a substrate having a surface, with said polymer material having said phosphorescent dye agent distributed therein formed as a coating thereon.

13. A pressure sensor as defined in claim 5 further comprising a substrate having a surface, with said polymer material having said phosphorescent dye agent distributed therein formed as a coating thereon.

14. A pressure sensor comprising a polymeric material having a backbone containing nitrogen, sulfur and phosphorous, the polymeric material having a phosphorescent dye agent distributed therein to detect changes in pressure, each of said sulfur and phosphorous having side groups selected from the group consisting of oxygen, a halogen, an aryloxy group, an alkoxy group, an arylamine group and an alkylamine group.

15. A pressure sensor as defined in claim 14 wherein said sulfur has a first side group including oxygen.

16. A pressure sensor as defined in claim 15 wherein said sulfur has a second side group that is a halogen.

17. A pressure sensor as defined in claim 16 wherein said sulfur has a second side group, and said phosphorous has first and second side groups which are the same as the second side group on sulfur.

18. A pressure sensor as defined in claim 14 wherein said phosphorous has first and second side groups and said sulfur has at least one side group, and the first and second side groups on phosphorous and the at least one side group on sulfur are selected from $NHBu^n$, $OBu^n$, $OC_6H_4$, $OC_6H_4CF_3$—m, $OCH_2CH=CH_2$, $OC_6H_4CF_3$—m and $OC_6H_4CF_3$—p.

19. A pressure sensor as defined in claim 18 wherein the first and second side groups on phosphorous and the second side group on sulfur are the same.

20. A pressure sensor as defined in claim 19 wherein said dye agent includes platinum or ruthenium.

21. A pressure sensor as defined in claim 20 wherein said dye agent includes Pt octaethylporphyrin, a $Ru^{II}$ bipyridyl, or $Ru^{II}$ phenanthroline.

22. A pressure sensor comprising a copolymeric material having a first polymer block having a backbone containing nitrogen and either sulfur or phosphorous or a combination thereof, the copolymeric material having a phosphorescent dye agent distributed therein, the pressure sensor being operable in an environment to sense changes in pressure therein.

23. A pressure sensor as defined in claim 22 wherein the first polymer block contains sulfur and wherein said sulfur is sulfur VI.

24. A pressure sensor as defined in claim 23, wherein said first polymer block terminates at said sulfur in an electron deficient state, said copolymeric material further comprising a second polymer block which includes at least one electron rich site.

25. A pressure sensor as defined in claim 24 wherein said at least one electron rich site includes oxygen or nitrogen.

26. A pressure sensor as defined in claim 25 wherein said second polymer block is formed by a ring opening polymerization of a cyclic group in the presence of said first polymer block, wherein said cyclic group is selected from the group consisting of a substituted or unsubstituted $C_{3-20}$ cycloalkyl group, a substituted or unsubstituted $C_{6-20}$ aryl group and a substituted or unsubstituted $C_{6-20}$ aralkyl group.

27. A pressure sensor as defined in claim 26 wherein said cyclic group is a $C_{3-5}$ cyclic group with an oxygen or nitrogen substituent in the ring.

28. A pressure sensor as defined in claim 26 wherein said cyclic group is tetrahydrofuran, ethylene oxide or propylene oxide.

29. A method of forming a pressure sensor, comprising the steps of:
   forming a mixture including a polymer having a backbone containing nitrogen and either sulfur or phosphorous or a combination thereof, together with a phosphorescent dye agent, said sensor being operatively characterized by a Stern Volmer plot having a linearity ranging from 0.985 to 1.0 and
   applying said mixture to a substrate.

30. A pressure sensor comprising a copolymer having a first polymer block having a backbone containing nitrogen, sulfur and phosphorous, and terminating at said sulfur in an electron deficient state, and a second polymer block having a backbone which includes at least one electron rich site, said pressure sensor further comprising a phosphorescent dye agent distributed in the copolymer.

31. A pressure sensor as defined in claim 30 wherein said sulfur is sulfur VI.

32. A pressure sensor as defined in claim 31 wherein said at least one electron rich site includes oxygen or nitrogen.

33. A pressure sensor as defined in claim 32, wherein said second polymer block is formed by a ring opening polymerization of a cyclic group in the presence of said first polymer block, the cyclic group being selected from the group consisting of a substituted or unsubstituted $C_{3-20}$ cycloalkyl group, a substituted or unsubstituted $C_{6-20}$ aryl group and a substituted or unsubstituted $C_{6-20}$ aralkyl group.

34. A pressure sensor as defined in claim 33 wherein said cyclic group is a $C_{3-5}$ cyclic group with an oxygen or nitrogen substituent in the ring.

35. A pressure sensor as defined in claim 34 wherein said cyclic group is tetrahydrofuran, ethylene oxide or propylene oxide.

36. A method of forming a pressure sensor comprising the steps of:
   providing a first polymer block having a backbone containing nitrogen, sulfur and phosphorous, and
   carrying out a ring opening polymerization of a cyclic group having at least one electron rich site therein, thereby to form a copolymer, and
   mixing said copolymer with a phosphorescent dye agent.

37. A method as defined in claim 36 wherein said ring opening polymerization step is carried out in the presence of said first polymer block.

38. A method as defined in claim 37 wherein said cyclic group is selected from the group consisting of a substituted or unsubstituted $C_{3-20}$ cycloalkyl group, a substituted or unsubstituted $C_{6-20}$ aryl group and a substituted or unsubstituted $C_{6-20}$ aralkyl group.

39. A method as defined in claim 38 wherein said cyclic group is a $C_{3-5}$ cyclic group with an oxygen or nitrogen substituent in the ring.

40. A method as defined in claim 39 wherein said cyclic group is tetrahydrofuran, ethylene oxide or propylene oxide.

41. A method of forming a pressure sensor, comprising the steps of:
   forming a mixture including a polymer having a backbone containing nitrogen and either sulfur or phosphorous or combinations thereof, together with a phosphorescent dye agent so as to form a polymer matrix with the phosphorescent dye agent therein; and
   processing the mixture into an operable form which, when exposed to an environment, will sense the presence of an oxygen partial pressure in the environment and be characterized by a Stern Volmer plot having a linearity of 0.985 to 1.0.

42. A method as defined in claim 41 wherein the Stern Volmer plot has a linearity ranging from 0.985 to 0.995.

43. A method as defined in claim 42 wherein the Stern Volmer plot has a linearity ranging from 0.990 to 0.995.

44. A method as defined in claim 41 wherein the Stern Volmer plot has a linearity ranging from 0.996 to 0.999.

45. A method of forming a pressure sensor, comprising the steps of:
   forming a mixture including a polymer having a backbone containing nitrogen and either sulfur or phosphorous or combinations thereof, together with a phosphorescent dye agent so as to form a polymer matrix with the phosphorescent dye agent therein; and
   processing the mixture into an operable form which, when exposed to an environment, will sense the presence of an oxygen partial pressure in the environment, and wherein said polymer matrix has a glass transition temperature ranging from −20° C. to 0° C.

46. A method as defined in claim 45 wherein said polymeric matrix has a glass transition temperature ranging from −17° C. to 0° C.

47. A method as defined in claim 46 wherein said polymeric matrix has a glass transition temperature of about −17° C.

* * * * *